(12) United States Patent
Wash et al.

(10) Patent No.: US 7,271,195 B2
(45) Date of Patent: *Sep. 18, 2007

(54) CARBONYL COMPOUNDS AS INHIBITORS OF HISTONE DEACETYLASE FOR THE TREATMENT OF DISEASE

(75) Inventors: Paul L. Wash, San Diego, CA (US); Brandon M. Wiley, Encinitas, CA (US); Christian Hassig, San Diego, CA (US); James W. Malecha, Libertyville, IL (US); Stewart A. Noble, San Diego, CA (US)

(73) Assignee: Kalypsys, Inc., San Diego, CA (US)

( * ) Notice: Subject to any disclaimer, the term of this patent is extended or adjusted under 35 U.S.C. 154(b) by 292 days.

This patent is subject to a terminal disclaimer.

(21) Appl. No.: 10/865,743

(22) Filed: Jun. 10, 2004

(65) Prior Publication Data

US 2005/0026907 A1    Feb. 3, 2005

Related U.S. Application Data

(60) Provisional application No. 60/477,721, filed on Jun. 10, 2003.

(51) Int. Cl.
*A61K 31/18* (2006.01)
*C07C 303/00* (2006.01)

(52) U.S. Cl. .................... 514/602; 564/84; 564/88
(58) Field of Classification Search ............ 564/84, 564/88; 514/602
See application file for complete search history.

(56) References Cited

U.S. PATENT DOCUMENTS

| | | | | |
|---|---|---|---|---|
| 3,632,345 A | * | 1/1972 | Marx et al. | 430/543 |
| 4,029,503 A | * | 6/1977 | Fujiwhara et al. | 430/226 |
| 4,129,656 A | | 12/1978 | Lang et al. | 424/263 |

FOREIGN PATENT DOCUMENTS

| EP | 0 055 458 A2 | 12/1981 |
|---|---|---|
| WO | WO 01/70675 A2 | 9/2001 |
| WO | WO 01/90100 A1 | 11/2001 |
| WO | WO 02/20500 A2 | 3/2002 |
| WO | WO 02/069947 A2 | 9/2002 |

OTHER PUBLICATIONS

Venkatesan et al., 1998, CAS: 129:230641.*
Fujiwara et al., 1975, CAS: 82:9982.*

* cited by examiner

*Primary Examiner*—Rebecca Anderson
*Assistant Examiner*—Rei-tsang Shiao
(74) *Attorney, Agent, or Firm*—Dennis A. Bennett; Cynthia Hathaway

(57) ABSTRACT

Disclosed herein are carbonyl compounds of Formula I, II, or III, and others as described herein.

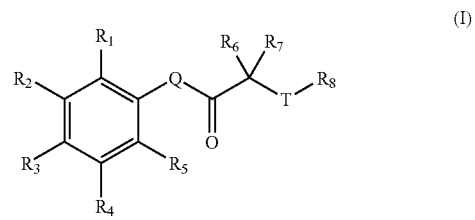

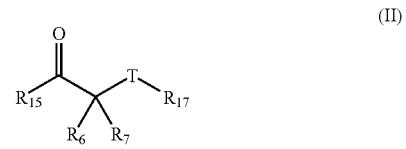

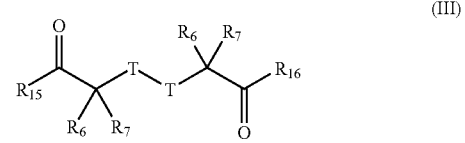

Also disclosed are methods of treating disease, such as cancer, neurological disorders, including polyglutamine-repeat disorders, anemias, thalassemias, inflammatory conditions, autoimmune diseases and cardiovascular conditions, using the compounds of the invention. In addition, methods of modulating the activity of histone deacetylase (HDAC) are also disclosed.

10 Claims, No Drawings

CARBONYL COMPOUNDS AS INHIBITORS OF HISTONE DEACETYLASE FOR THE TREATMENT OF DISEASE

CROSS REFERENCE TO RELATED APPLICATION

This Application claims priority of U.S. provisional application Ser. No. 60/477,721, filed Jun. 10, 2003.

FIELD OF THE INVENTION

The present invention is directed to carbonyl compounds as inhibitors of histone deacetylase (HDAC). These compounds are useful in treatments of disease states, including, but not limited to, certain cancers (such as colon cancer, breast cancer, ovarian cancer, lung cancer, prostate cancer, cancers of the pancreas, cervix, uteri, kidney, brain and central nervous system, non-Hodgkin's lymphoma, multiple myeloma and hematopoietic malignancies including leukemias (Chronic Lymphocytic Leukemia) and lymphomas), neurological disorders, including polyglutamine-repeat disorders (such as Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA) and Dentatorubral pallidolusyian atrophy (DRPLA), anemias and thalassemia (such as Sickle Cell Disease (SCD), inflammatory conditions (such as Rheumatoid Arthritis (RA), Inflammatory Bowel Disease (IBD), ulcerative colitis and psoriasis) autoimmune diseases (such as Systemic Lupus Erythromatosus (SLE) and Multiple Sclerosis (MS)) and cardiac hypertrophy and heart failure.

BACKGROUND OF THE INVENTION

Histone proteins organize DNA into nucleosomes, which are regular repeating structures of chromatin. The acetylation status of histones alters chromatin structure, which, in turn, is involved in gene expression. Two classes of enzymes can affect the acetylation of histones —histone acetyltransferases (HATs) and histone deacetylases (HDACs). A number of HDAC inhibitors have been characterized. However, to date no effective candidate for cancer therapy has been identified. Therefore, there is a need in the art to discover HDAC inhibitors that have effective anti-tumor activity.

SUMMARY OF THE INVENTION

Disclosed herein are carbonyl compounds of Formula I, II, or III and related Formulae IV, V, VI VII, or VIII, as described herein, including their pharmaceutically acceptable salts, esters, and prodrugs.

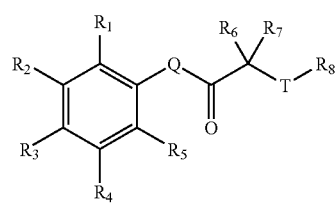

(I)

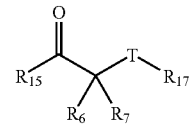

(II)

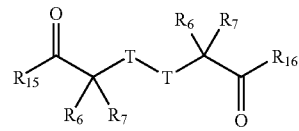

(III)

Also disclosed are pharmaceutical compositions comprising a compound having structural formulae I, II, III, IV, V, VI, VII or VIII which are capable of inhibiting the catalytic activity of histone deacetylase (HDAC).

Also disclosed are methods of treating diseases in mammals, including humans, such as cancer, using the compounds of the invention. In addition, methods of modulating the activity of histone deacetylase (HDAC) are also disclosed.

DETAILED DESCRIPTION OF THE PREFERRED EMBODIMENT

An aspect of the present invention relates to a compound of Formula I

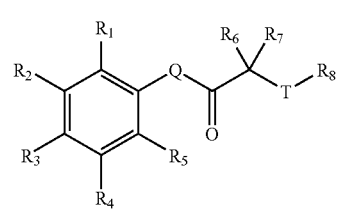

(I)

or a pharmaceutically acceptable salt, amide, ester, or prodrug thereof, wherein a) $R_1$-$R_5$ is each independently selected from the group consisting of
   i) hydrogen;
   ii) lower alkyl;
   iii) lower alkylene;
   iv) halogen or perhaloalkyl;
   v) an alkoxy of formula —$(X_1)_{n1}$—O—$X_2$, where
      $X_1$ is selected from the group consisting of lower alkylene, lower alkenylene, lower alkynylene, aryl, and heteroaryl;
      $X_2$ is selected from the group consisting of hydrogen, lower alkyl, lower perfluoroalkyl, aryl, and heteroaryl; and
      n1 is 0, 1, 2, or 3; and
   vi) a five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of
      A) optionally substituted $C_1$-$C_8$ straight-chain, branched, or cyclic saturated or unsaturated alkyl;

B) an alkoxy of formula —$(X_1)_{n1}$—O—$X_2$, where
  $X_1$ is selected from the group consisting of lower alkylene, lower alkenylene, lower alkynylene, aryl, and heteroaryl;
  $X_2$ is selected from the group consisting of hydrogen, lower alkyl, lower perfluoroalkyl, aryl, and heteroaryl; and
  n1 is 0, 1, 2, or 3;
C) halogen or perhaloalkyl;
D) cyano;
E) nitro;
F) an amino of formula —$(X_3)_{n3}$—$NX_4X_5$, where
  $X_3$ is selected from the group consisting of lower alkylene, lower alkenylene, lower alkynylene, aryl, and heteroaryl;
  $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
  n3 is 0 or 1;
G) a thioether or thiol of formula —$(X_6)_{n6}$—S—$X_7$, where
  $X_6$ is selected from the group consisting of lower alkylene, lower alkenylene, lower alkynylene, aryl, and heteroaryl;
  $X_7$ is selected from the group consisting of hydrogen, lower alkyl, lower perfluoroalkyl, aryl, and heteroaryl; and
  n6 is 0, 1, 2, or 3; and
H) an amide of formula —$(X_7)_{n7}$—NH—C(O)—$X_8$ or —$(X_9)_{n9}$—C(O)—NH—$X_{10}$
  $X_7$ and $X_9$ are each independently selected from the group consisting of lower alkylene, lower alkenylene, lower alkynylene, aryl, and heteroaryl;
  $X_8$ is selected from the group consisting of hydrogen, lower alkyl, lower alkenyl, heteroalkyl, aryl, heteroaryl, hydroxy, alkoxy, and amide; and
  $X_{10}$ is selected from the group consisting of hydrogen, lower alkyl, lower alkenyl, heteroalkyl, aryl, and heteroaryl;
  n7 and n9 are each independently is 0 or 1;
vii) an acyl of formula —$(X_1)_{n1}$—C(O)—$X_2$, where
  $X_1$ is selected from the group consisting of lower alkylene, lower alkenylene, lower alkynylene, aryl, and heteroaryl;
  $X_2$ is selected from the group consisting of hydrogen, lower alkyl, aryl, heteroaryl, hydroxy, alkoxy, amino, and —NH—$X_3$,
    where $X_3$ is selected from the group consisting of hydrogen, alkyl, aryl, heteroaryl, amino, and amide; and
  n1 is 0, 1, 2, or 3; and
viii) cyano;
ix) nitro;
x) an amino of formula —$(X_{15})_{n15}$—$NX_{16}X_{17}$, where
  $X_{15}$ is selected from the group consisting of lower alkylene, lower alkenylene, lower alkynylene, aryl, and heteroaryl;
  $X_{16}$ and $X_{17}$ are each independently selected from the group consisting of hydrogen, lower alkyl, aryl, and heteroaryl; or $X_{16}$ and $X_{17}$, taken together with the nitrogen to which they are attached, form a five-membered or six-membered heteroaromatic or heteroaliphatic ring; and
  n15 is 0 or 1;
xi) thioether or thiol of formula —$(X_{22})_{n22}$—S—$X_{23}$, where
  $X_{22}$ is selected from the group consisting of lower alkylene, lower alkenylene, lower alkynylene, aryl, and heteroaryl;
  $X_{23}$ is selected from the group consisting of hydrogen, lower alkyl, lower perfluoroalkyl, aryl, and heteroaryl; and
  n22 is 0, 1, 2, or 3;
xii) an N-sulfonamido of structure $$R_{18}-\underset{\underset{O}{\|}}{\overset{\overset{O}{\|}}{S}}-\underset{R_{20}}{N}\diagup$$

wherein
$R_{18}$ is a lower alkyl, lower heteroalkyl, or is a five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of
A) optionally substituted $C_1$-$C_8$ straight-chain, branched, or cyclic saturated or unsaturated alkyl;
B) an alkoxy of formula —$(X_1)_{n1}$—O—$X_2$, where
  $X_1$ is selected from the group consisting of lower alkylene, lower alkenylene, lower alkynylene, aryl, and heteroaryl;
  $X_2$ is selected from the group consisting of hydrogen, lower alkyl, perhalolkyl, aryl, and heteroaryl; and
  n1 is 0, 1, 2, or 3;
C) halogen or perhaloalkyl;
D) cyano;
E) nitro;
F) an amino of formula —$(X_3)_{n3}$—$NX_4X_5$, where
  $X_3$ is selected from the group consisting of lower alkylene, lower alkenylene, lower alkynylene, aryl, and heteroaryl;
  $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
  n3 is 0, or 1;
G) a thioether or thiol of formula —$(X_6)_{n6}$—S—$X_7$, where
  $X_6$ is selected from the group consisting of lower alkylene, lower alkenylene, lower alkynylene, aryl, and heteroaryl;
  $X_7$ is selected from the group consisting of hydrogen, lower alkyl, aryl, heteroaryl, and perfluoroalkyl; and
  n6 is 0, 1, 2, or 3; and
H) an amide of formula —$(X_7)_{17}$—NH—C(O)—$X_8$ or —$(X_9)_{n9}$—C(O)—NH—$X_{10}$
  $X_7$ and $X_9$ are each independently selected from the group consisting of lower alkylene, lower alkenylene, lower alkynylene, aryl, and heteroaryl;

$X_8$ is selected from the group consisting of hydrogen, lower alkyl, lower alkenyl, aryl, heteroaryl, heteroalkyl, hydroxy, alkoxy, and amide; and $X_{10}$ is selected from the group consisting of hydrogen, lower alkyl, lower alkenyl, aryl, and heteroaryl, and heteroalkyl;

n7 and n9 are each independently is 0 or 1;

$R_{20}$ is H, lower alkyl, lower aralkyl, or $R_{20}$ taken together with $R_{18}$ forms an optionally substituted five-, six-, seven-, or eight-membered heterocyclic ring, as shown below:

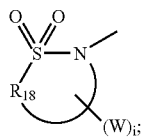

and wherein i is 0, 1, 2, 3, 4;

xiii) an S-sulfonamido of formula

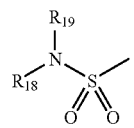

wherein $R_{18}$ is lower alkyl, lower heteroalkyl, or a five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of A) optionally substituted $C_1$-$C_8$ straight-chain, branched, or cyclic saturated or unsaturated alkyl;

B) an alkoxy of formula —$(X_1)_{n1}$—O—$X_2$, where
$X_1$ is selected from the group consisting of lower alkylene, lower alkenylene, lower alkynylene, aryl, and heteroaryl;
$X_2$ is selected from the group consisting of hydrogen, lower alkyl, perhaloalkyl, aryl, and heteroaryl; and
n1 is 0, 1, 2 or 3:

C) halogen or perhaloalkyl;

D) cyano;

E) nitro;

F) an amino of formula —$(X_3)_{n3}$—$NX_4X_5$, where
$X_3$ is selected from the group consisting of lower alkylene, lower alkenylene, lower alkynylene, aryl, and heteroaryl;
$X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
n3 is 0 or 1;

G) a thioether or thiol of formula —$(X_6)_{n6}$—S—$X_7$, where
$X_6$ is selected from the group consisting of lower alkylene, lower alkenylene, lower alkynylene, aryl, and heteroaryl;
$X_7$ is selected from the group consisting of hydrogen, lower alkyl, aryl, perfluoroalkyl, and heteroaryl; and
n6 is 0, 1, 2, or 3; and H) an amide of formula —$(X_7)_{n7}$—NH—C(O)—$X_8$ or —$(X_9)_{n9}$—C(O)—NH—$X_{10}$
$X_7$ and $X_9$ are each independently selected from the group consisting of lower alkylene, lower alkenylene, lower alkynylene, aryl, and heteroaryl;
$X_8$ is selected from the group consisting of hydrogen, lower alkyl, lower alkenyl, aryl, heteroaryl, hydroxy, alkoxy, and amide; and
$X_{10}$ is selected from the group consisting of hydrogen, lower alkyl, lower alkenyl, aryl, and heteroaryl;
n7 and n9 are each independently is 0 or 1;

$R_{19}$ is H, $C_{1-5}$ alkyl, $C_{1-5}$ aralkyl, or taken together with one of $R_1$, $R_2$, $R_3$, $R_4$, or $R_5$, said $R_{19}$ forms an optionally substituted five-, six-, seven-, or eight-membered heterocyclic ring, as shown below:

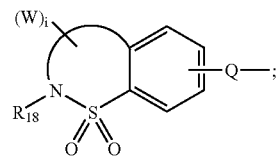

i is 0, 1, 2, 3, 4;

or $R_1$ and $R_2$, taken together along with the two ring carbons to which they are attached, or $R_2$ and $R_3$, taken together along with the two ring carbons to which they are attached, or $R_3$ and $R_4$, taken together along with the two ring carbons to which they are attached, or $R_4$ and $R_5$, taken together along with the two ring carbons to which they are attached, form a five-, six-, seven-, or eight-membered carbocyclic or heterocyclic aliphatic ring, or a six-membered aromatic or heteroaromatic, or a five- or six-membered heteroaromatic ring, each of which is optionally substituted with one or more substituents, W, each of which is independently selected from the group consisting of i) hydrogen;

ii) optionally substituted $C_1$-$C_8$ straight-chain, branched, or cyclic saturated or unsaturated alkyl;

iii) optionally substituted aryl;

iv) optionally substituted heterocyclyl;

v) an alkoxy of formula —$(X_{13})_{n13}$—O—$X_{14}$, where
$X_{13}$ is selected from the group consisting of lower alkylene, lower alkenylene, lower alkynylene, aryl, and heteroaryl;
$X_{14}$ is selected from the group consisting of hydrogen, lower alkyl, aryl, perhaloalkyl, and heteroaryl; and
n13 is 0, 1, 2, or 3;

vi) halogen or perhaloalkyl;

vii) cyano;

viii) nitro;

ix) an amino of formula —$(X_{15})_{n15}$—$NX_{16}X_{17}$, where
$X_{15}$ is selected from the group consisting of lower alkylene, lower alkenylene, lower alkynylene, aryl, and heteroaryl;
$X_{16}$ and $X_{17}$ are each independently selected from the group consisting of hydrogen, lower alkyl, aryl, and heteroaryl; or $X_{16}$ and $X_{17}$, taken together with the nitrogen to which they are attached, form a five-membered or six-membered heteroaromatic or heteroaliphatic ring; and n15 is 0 or 1; and x) a thioether or thiol of formula —$(X_{22})_{n22}$—S—$X_{23}$, where $X_{22}$ is selected from the group consisting of lower alkylene, lower alkenylene, lower alkynylene, aryl, and heteroaryl;

$X_{23}$ is selected from the group consisting of hydrogen, lower alkyl, perfluoroalkyl, aryl, and heteroaryl; and n22 is 0, 1, 2, or 3;

xxii) an S-sulfonamido of formula

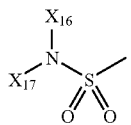

wherein $X_{16}$ and $X_{17}$ are each independently selected from the group consisting of hydrogen, lower alkyl, lower heteroalkyl, optionally substituted aryl, and optionally substituted heteroaryl; and xxiii) an N-sulfonamido of structure

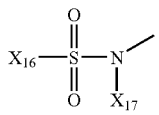

wherein $X_{16}$ and $X_{17}$ are each independently selected from the group consisting of hydrogen, lower alkyl, lower heteroalkyl, optionally substituted aryl, and optionally substituted heteroaryl;

b) $R_6$ and $R_7$ are each independently selected from the group consisting of hydrogen and lower alkyl;

c) $R_8$ is selected from the group consisting of
  i) hydrogen;
  ii) optionally substituted $C_1$-$C_8$ straight-chain, branched, or cyclic saturated or unsaturated alkyl;
  iii) cyano;
  iv)

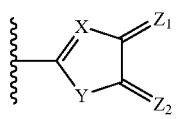

wherein
  X is selected from CH and nitrogen;
  Y is selected from the group consisting of $CH_2$, NH, oxygen and sulfur;
  $Z_1$ and $Z_2$ are each independently selected from the group consisting of null, oxygen, sulfur, and $CR_{11}R_{12}$,
  wherein $R_{11}$ and $R_{12}$ are each independently selected from the group consisting of hydrogen, lower alkyl, lower alkoxy, aryl, aryloxy, $NH_2$, halogen, perhaloalkyl, and hydroxy; and v)

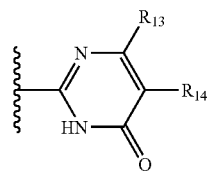

wherein $R_{13}$ and $R_{14}$ are each independently selected from the group consisting of hydrogen, lower alkyl, lower alkoxy, aryl, aryloxy, $NH_2$, halogen, perhaloalkyl, and hydroxy;

vi) optionally substituted acyl, —C(O)$R_E$, wherein HOC(O)$R_E$ is any pharmaceutically acceptable acid;

vii) or $R_8$ is equivalent to the balance of Formula I to form a disulfide dimer;

d) Q is selected from the group consisting of a bond, oxygen, sulfur, —$(CH_2)_m$—, —$(CH_2)_m$NH—, —$(CH_2)_m$(CO)—, —$(CH_2)_m$NH(CO)—, and —$(CH_2)_m$C(O)NH—, wherein m is 0-7, wherein if Q is not symmetric, Q may be attached in either direction; and e) T is selected from the group consisting of oxygen, sulfur, and —$NR_{17}$, wherein $R_{17}$ is selected from the group consisting of hydrogen, lower alkyl, and aryl.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The terms "physiologically acceptable" and "physiologically compatible" refers to excipients, products, or hydrolysis products of disclosed molecular embodiments of the invention. By way of example, protected thiol prodrug embodiments may release acids upon hydrolysis of the protected thiol. Physiologically acceptable excipients and acids are those that do not abrogate the biological activity or properties of the compound, and are nontoxic. "Physiologically acceptable" and "pharmaceutically acceptable" may be coextensive terms.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "lower perfluoroalkoxy" refers to a radical —O—$(CX_2)_nCX_3$ where X is any halogen, preferable F or Cl, and n is 1-5.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Yet another example of a prodrug are protected thiol compounds. Thiols bearing hydrolyzable protecting groups can unmask protected SH groups prior to or simultaneous to use.

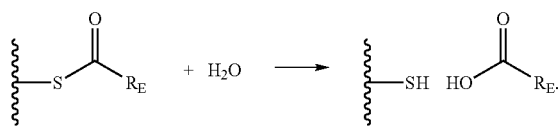

The term thiol protecting group refers to thiols bearing hydrolyzable protecting groups that can unmask protected SH groups prior to or simultaneous to use. Preferred thiol protecting groups include but are not limited to thiol esters which release pharmaceutically acceptable acids along with an active thiol moiety. Such pharmaceutically acceptable acids are generally nontoxic and do not abbrogate the biological activity of the active thiol moiety. Examples of pharmaceutically acceptable acids include, but are not limited to:

N,N-diethylglycine;

4-ethylpiperazinoacetic acid;

ethyl 2-methoxy-2-phenylacetic acid;

N,N-dimethylglycine;

(nitrophenoxysulfonyl)benzoic acid;

Acetic acid;

Maleic acid;

Fumaric acid;

Benzoic acid;

Tartraric acid;

Natural amino acids (like glutamate, aspartate, cyclic aminoacids such praline);

D-amino acids;

Butyric acid;

Fatty acids like palmitic acid, stearic acid, oleate;

Pipecolic acid;

Phosphonic acid;

Phosphoric acid;

pivalate (trimethylacetic acid);

Succinic acid;

Cinnamic acid;

Anthranilic acid;

Salicylic acid;

Lactic acid; and

Pyruvic acids.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" or "heteroaryl" refers to an aromatic group which contains at least one heterocyclic ring.

A carbocyclic or heterocyclic ring may be aliphatic. In this case, the ring is either completely saturated, or if there is unsaturation, the conjugation of the pi-electrons in the ring do not give rise to aromaticity. The term "heterocyclyl" thus refers to a heterocyclic aliphatic or a heterocyclic aromatic (i.e., a heteroaryl) ring. Likewise, the term "carbocyclyl" refers to a carbocyclic aliphatic or a carbocyclic aromatic (i.e., an aryl) ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 4 carbon atoms. The alkyl group of the compounds of the invention may be designated as "$C_1$-$C_5$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The substituent "R" appearing by itself and without a number designation refers to a substituent selected from the group consisting of optionally substituted alkyl, optionally substituted cycloalkyl, optionally substituted aryl, optionally substituted heteroaryl (bonded through a ring carbon) and optionally substituted heteroalicyclic (bonded through a ring carbon).

An "O-carboxy" group refers to a RC(=O)O— group, where R is as defined herein.

A "C-carboxy" group refers to a —C(=O)OR groups where R is as defined herein.

An "acyl" group refers to a —C(=O)R group.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term partially halogenated alkyl refers to an alkyl group having both hydrogen and halogen substituents.

The term "perhaloalkyl" refers to an alkyl group where all of the hydrogen atoms are replaced by halogen atoms.

When two substituents taken together along with the two ring carbons to which they are attached form a ring, it is meant that the following structure:

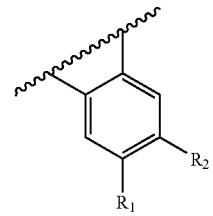

is, for example, representative of a structure such as the following:

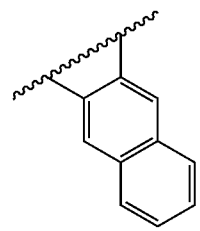

In the above example, R$_1$ and R$_2$, taken together along with the two ring carbons to which they are attached, form a six-membered aromatic ring.

Unless otherwise indicated, when a substituent is deemed to be "optionally substituted," it is meant that the substituent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In certain embodiments, the invention relates to a compound of Formula I where R$_1$-R$_5$ are hydrogen.

In other embodiments R$_2$ is an alkoxy. The alkoxy may be selected from the group consisting of methoxy, ethoxy, propoxy, n-butoxy, t-butoxy, and isobutoxy. In some embodiments, R$_3$ is an alkoxy.

In certain embodiments, R$_3$ is a halogen. "Halogen" refers to a substituent selected from the group consisting of fluorine, chlorine, bromine, and iodine. Thus, in some embodiments the halogen may be chlorine, whereas in other embodiments, the halogen may be bromine. In still other embodiments, R$_3$ is a perhaloalkyl. The perhaloalkyl may be selected from the group consisting of trifluoromethyl, pentafluoroethyl, and heptafluoropropyl.

In some embodiments, R$_3$ is a heterocyclyl. The heterocyclyl may be selected from the group consisting of furan, thiophene, pyrrole, pyrroline, pyrrolidine, oxazole, thiazole, imidazole, imidazoline, imidazolidine, pyrazole, pyrazoline, pyrazolidine, isoxazole, isothiazole, triazole, thiadiazole, pyran, pyridine, piperidine, morpholine, thiomorpholine, pyridazine, pyrimidine, pyrazine, piperazine, triazine,

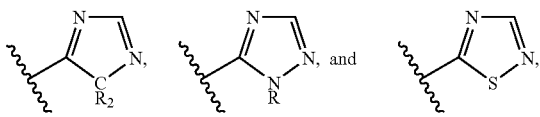

where R is as defined herein. In some embodiments the heterocyclyl is pyrrolidine, whereas in other embodiments, the heterocyclyl is morpholine.

In certain embodiments, $R_3$ is —NH(CO)R, where R is as defined herein. In some embodiments, R is selected from hydrogen, and lower alkyl, where the alkyl may be selected from the group consisting of methyl, ethyl, propyl, n-butyl, t-butyl, and isobutyl.

In some embodiments, $R_2$ and $R_3$, taken together along with the two ring carbons to which they are attached form a six-membered heterocyclic ring. In certain of these embodiments, the six-membered heterocyclic ring has the following structure:

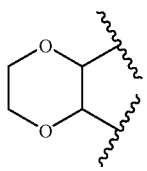

Thus, in some embodiments, the compound of Formula I will have the following structure:

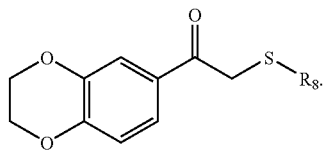

In some embodiments $R_3$ or $R_4$ is an optionally substituted N-sulfonamido or an optionally substituted S-sulfonamido.

In some embodiments $R_3$ or $R_4$ has the structure

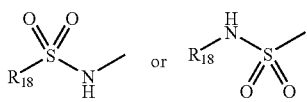

wherein $R_{18}$ is selected from the group consisting of optionally substituted aryl and optionally substituted heteroaryl.

In some embodiments $R_{18}$ is phenyl, singly or multiply substituted with $C_{1-5}$ alkyl, $C_{1-5}$ perhaloalkyl, $C_{1-5}$ alkoxy, $C_{1-5}$ perhaloalkyl alkoxy, and N-alkylamido.

In some embodiments $R_6$ and $R_7$ are hydrogen.

In certain embodiments, $R_8$ is cyano. In other embodiments, $R_8$ is

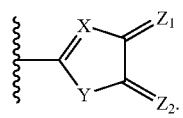

In some of these embodiments, X is nitrogen, Y is oxygen and $Z_1$ and $Z_2$ are $H_2$, whereas in other embodiments, X is nitrogen, Y is NH, $Z_1$ is oxygen and $Z_2$ is $H_2$. In still other embodiments, X is nitrogen, Y is NH, and Z, and $Z_2$ are oxygen, while in other embodiments, X is nitrogen, Y is sulfur, $Z_1$ is (H)(OH) and $Z_2$ is $H_2$.

When $Z_1$ or $Z_2$ are $H_2$, it is meant that the ring carbon to which $Z_1$ or $Z_2$ are attached forms a methylene (—CH$_2$—) group. When $Z_1$ or $Z_2$ are oxygen, it is meant that the ring carbon to which $Z_1$ or $Z_2$ are attached forms a carbonyl (—C(O)—) group. When $Z_1$ or $Z_2$ are (H)(OH), it is meant that the ring carbon to which $Z_1$ or $Z_2$ are attached forms a hydroxymethylene (—CH(OH)—) group.

In certain other embodiments, $R_8$ is

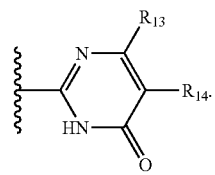

In some of these embodiments, $R_{13}$ and $R_{14}$ are hydrogen, whereas in other embodiments, $R_{13}$ is lower alkyl and $R_{14}$ are hydrogen, where the alkyl may be selected from the group consisting of methyl, ethyl, propyl, n-butyl, t-butyl, and isobutyl.

In certain embodiments, the present invention relates to a compound of Formula I where T is sulfur. In other embodiments, T is oxygen, whereas in yet other embodiments, T is —NR.

In another aspect, the present invention relates to a compound of Formula II or III,

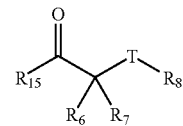

(II)

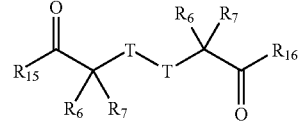

(III)

or a pharmaceutically acceptable salt, amide, ester, or prodrug thereof, or a pharmaceutical composition comprising such compounds, wherein a) T is selected from the group consisting of oxygen, sulfur, and —NR$_{17}$, wherein $R_{17}$ is selected from the group consisting of hydrogen, lower alkyl, and aryl;

b) $R_{15}$ and $R_{16}$ are each independently selected from the group consisting of
  i) an alkoxy of formula —(X$_1$)$_{n1}$—O—X$_2$, where
    $X_1$ is selected from the group consisting of lower alkylene, lower alkenylene, lower alkynylene, aryl, and heteroaryl;
    $X_2$ is selected from the group consisting of hydrogen, lower alkyl, lower perfluoroalkyl, aryl, and heteroaryl; and
    n1 is 0, 1, 2, or 3; and
  ii) a five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of
A) optionally substituted $C_1$-$C_8$ straight-chain, branched, or cyclic saturated or unsaturated alkyl;
B) an alkoxy of formula —$(X_1)_{n1}$—O—$X_2$, where
   $X_1$ is selected from the group consisting of lower alkylene, lower alkenylene, lower alkynylene, aryl, and heteroaryl;
   $X_2$ is selected from the group consisting of hydrogen, lower alkyl, lower perhaloalkyl, aryl, and heteroaryl; and
   n1 is 0, 1, 2 or 3
C) halogen or perhaloalkyl;
D) cyano;
E) nitro;
F) an amino of formula —$(X_3)_{n3}$—$NX_4X_5$, where
   $X_3$ is selected from the group consisting of lower alkylene, lower alkenylene, lower alkynylene, aryl, and heteroaryl;
   $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
   n3 is 0 or 1;
G) a thioether or thiol of formula —$(X_6)_{n6}$—S—$X_7$, where
   $X_6$ is selected from the group consisting of lower alkylene, lower alkenylene, lower alkynylene, aryl, and heteroaryl;
   $X_7$ is selected from the group consisting of hydrogen, lower alkyl, lower perhaloalkyl, aryl, and heteroaryl; and
   n6 is 0, 1, 2, or 3; and
H) an amide of formula —$(X_7)_{n7}$—NH—C(O)—$X_8$ or —$(X_9)_{n9}$—C(O)—NH—$X_{10}$
   $X_7$ and $X_9$ are each independently selected from the group consisting of lower alkylene, lower alkenylene, lower alkynylene, aryl, and heteroaryl;
   $X_8$ is selected from the group consisting of hydrogen, lower alkyl, lower alkenyl, lower heteroalkyl, aryl, heteroaryl, hydroxy, alkoxy, and amide; and
   $X_{10}$ is selected from the group consisting of hydrogen, lower alkyl, lower alkenyl, lower heteroalkyl, aryl, and heteroaryl;
   n7 and n9 are each independently is 0 or 1;
I) an N-sulfonamido of structure

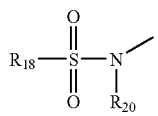

wherein
$R_{18}$ is a lower alkyl, lower heteroalkyl, or five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of
(1) optionally substituted $C_1$-$C_8$ straight-chain, branched, or cyclic saturated or unsaturated alkyl;
(2) an alkoxy of formula —$(X_1)_{n1}$—O—$X_2$, where
   $X_1$ is selected from the group consisting of lower alkylene, lower alkenylene, lower alkynylene, aryl, and heteroaryl;
   $X_2$ is selected from the group consisting of hydrogen, lower alkyl, lower perhaloalkyl, aryl, and heteroaryl; and
   n1 is 0, 1, 2 or 3;
(3) halogen or perhaloalkyl;
(4) cyano;
(5) nitro;
(6) an amino of formula —$(X_3)_{n3}$—$NX_4X_5$, where
   $X_3$ is selected from the group consisting of lower alkylene, lower alkenylene, lower alkynylene, aryl, and heteroaryl;
   $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
   n3 is 0 or 1;
(7) a thioether or thiol of formula —$(X_6)_{n6}$—S—$X_7$, where
   $X_6$ is selected from the group consisting of lower alkylene, lower alkenylene, lower alkynylene, aryl, and heteroaryl;
   $X_7$ is selected from the group consisting of hydrogen, lower alkyl, perfluoroalkyl, aryl, and heteroaryl; and
   n6 is 0, 1, 2, or 3; and
(8) an amide of formula —$(X_7)_{n7}$—NH—C(O)—$X_8$ or —$(X_9)_{n9}$—C(O)—NH—$X_{10}$
   $X_7$ and $X_9$ are each independently selected from the group consisting of lower alkylene, lower alkenylene, lower alkynylene, aryl, and heteroaryl;
   $X_8$ is selected from the group consisting of hydrogen, lower alkyl, lower alkenyl, aryl, lower heteroalkyl, heteroaryl, hydroxy, alkoxy, and amide; and
   $X_{10}$ is selected from the group consisting of hydrogen, lower alkyl, lower alkenyl, aryl, lower heteroalkyl, and heteroaryl;
   n7 and n9 are each independently is 0 or 1;
$R_{20}$ is H, $C_{1-5}$ alkyl, $C_{1-5}$ aralkyl, or taken together with $R_{18}$ forms an optionally substituted five-, six-, seven-, or eight-membered heterocyclic ring, having the following structure:

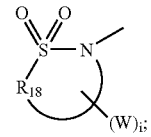

i is 0, 1, 2, 3, 4;
J) an S-sulfonamido of formula

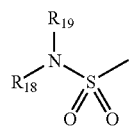

wherein $R_{18}$ is a lower alkyl, lower heteroalkyl, or five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of (1) optionally substituted $C_1$-$C_8$ straight-chain, branched, or cyclic saturated or unsaturated alkyl;
(2) an alkoxy of formula —$(X_1)_{n1}$—O—$X_2$, where
   $X_1$ is selected from the group consisting of lower alkylene, lower alkenylene, lower alkynylene, aryl, and heteroaryl;
   $X_2$ is selected from the group consisting of hydrogen, lower alkyl, perhaloalkyl, aryl, and heteroaryl; and
   n1 is 0, 1, 2, or 3
(3) halogen or perhaloalkyl;
(4) cyano;
(5) nitro;
(6) an amino of formula —$(X_3)_{n3}$—$NX_4X_5$, where
   $X_3$ is selected from the group consisting of lower alkylene, lower alkenylene, lower alkynylene, aryl, and heteroaryl;
   $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
   n3 is 0 or 1;
(7) a thioether or thiol of formula —$(X_6)_{n6}$—S—$X_7$, where
   $X_6$ is selected from the group consisting of lower alkylene, lower alkenylene, lower alkynylene, aryl, and heteroaryl;
   $X_7$ is selected from the group consisting of hydrogen, lower alkyl, lower perfluoroalkyl, aryl, and heteroaryl; and
   n6 is 0, 1, 2, or 3; and
(8) an amide of formula —$(X_7)_{n7}$—NH—C(O)—$X_8$ or —$(X_9)_{n9}$—C(O)—NH—$X_{10}$
   $X_7$ and $X_9$ are each independently selected from the group consisting of lower alkylene, lower alkenylene, lower alkynylene, aryl, and heteroaryl;
   $X_8$ is selected from the group consisting of hydrogen, lower alkyl, lower alkenyl, aryl, heteroaryl, hydroxy, alkoxy, and amide; and
   $X_{10}$ is selected from the group consisting of hydrogen, lower alkyl, lower alkenyl, aryl, and heteroaryl;
   n7 and n9 are each independently is 0 or 1;
wherein $R_{19}$ is H, $C_{1-5}$ alkyl, $C_{1-5}$ aralkyl, or $R_{19}$ taken together with a portion of the ring to which the S of the S-sulfonamido attaches forms an optionally substituted five-, six-, seven-, or eight-membered heterocyclic ring, as shown below:

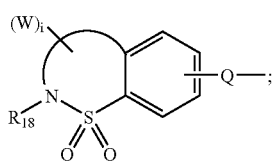

wherein W is independently selected from the group consisting of
(1) hydrogen;
(2) optionally substituted $C_1$-$C_8$ straight-chain, branched, or cyclic saturated or unsaturated alkyl;
(3) optionally substituted aryl;
(4) optionally substituted heterocyclyl;
(5) an alkoxy of formula —$(X_{13})_{n13}$—O—$X_{14}$, where
   $X_{13}$ is selected from the group consisting of lower alkylene, lower alkenylene, lower alkynylene, aryl, and heteroaryl;
   $X_{14}$ is selected from the group consisting of hydrogen, lower alkyl, aryl, lower perhaloalkyl, and heteroaryl; $n_{13}$=0, 1, 2, or 3; and
wherein i is 0, 1, 2, 3, 4;
iii) an acyl of formula —$(X_1)_{n1}$—C(O)—$X_2$, where
   $X_1$ is selected from the group consisting of lower alkylene, lower alkenylene, lower alkynylene, aryl, and heteroaryl;
   $X_2$ is selected from the group consisting of hydrogen, lower alkyl, aryl, heteroaryl, hydroxy, alkoxy, amino, and —NH—$X_3$,
      where $X_3$ is selected from the group consisting of hydrogen, alkyl, aryl, heteroaryl, amino, and amide; and
   n1 is 0, 1, 2 or 3; and
iv) cyano;
v) nitro;
vi) an amino of formula —$(X_{15})_{n15}$—$NX_{16}X_{17}$, where
   $X_{15}$ is selected from the group consisting of lower alkylene, lower alkenylene, lower alkynylene, aryl, and heteroaryl;
   $X_{16}$ and $X_{17}$ are each independently selected from the group consisting of hydrogen, lower alkyl, aryl, and heteroaryl; or $X_{16}$ and $X_{17}$, taken together with the nitrogen to which they are attached, form a five-membered or six-membered heteroaromatic or heteroaliphatic ring; and
   n15 is 0 or 1; and
vii) a thioether or thiol of formula —$(X_{22})_{n22}$—S—$X_{23}$, where
   $X_{22}$ is selected from the group consisting of lower alkylene, lower alkenylene, lower alkynylene, aryl, and heteroaryl;
   $X_{23}$ is selected from the group consisting of hydrogen, lower alkyl, lower perfluoralkyl, aryl, and heteroaryl; and
   n22 is 0, 1, 2, or 3 and c) $R_8$ is selected from the group consisting of
   i) hydrogen;
   ii) optionally substituted $C_1$-$C_8$ straight-chain, branched, or cyclic saturated or unsaturated alkyl;
   iii) cyano;

iv)

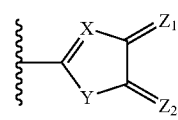

wherein
X is selected from CH and nitrogen;

Y is selected from the group consisting of CH$_2$, NH, oxygen and sulfur;

Z$_1$ and Z$_2$ are each independently selected from the group consisting of null, oxygen, sulfur, and CR$_{11}$R$_{12}$, wherein R$_{11}$ and R$_{12}$ are each independently selected from the group consisting of hydrogen, lower alkyl, lower alkoxy, aryl, aryloxy, NH$_2$, halogen, perhaloalkyl, and hydroxy; and v)

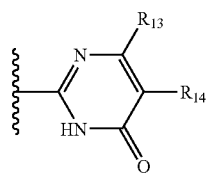

wherein R$_{13}$ and R$_{14}$ are each independently selected from the group consisting of hydrogen, lower alkyl, lower alkoxy, aryl, aryloxy, NH$_2$, halogen, perhaloalkyl, and hydroxy;

vi) optionally substituted acyl of the formula —OC(O)R$_E$, wherein HOC(O)R$_E$ is a pharmaceutically acceptable acid;.

d) R$_6$ and R$_7$ are each independently selected from the group consisting of hydrogen and lower alkyl.

In certain embodiments, R$_{15}$ and R16 are independently selected from the group consisting of an optionally substituted five-, six-, seven-, or eight-membered carbocyclic or heterocyclic ring, five-membered or six-membered heteroaryl ring, or six-membered aryl or heteroaryl ring.

In some embodiments, R$_{16}$ is selected from the group consisting of hydrogen, lower alkyl, and aryl.

In certain embodiments, the present invention relates to a compound of Formula II or III where T is sulfur. In other embodiments, T is oxygen, whereas in yet other embodiments, T is —NR.

In another aspect, the invention relates to a compound selected from the group consisting of the compounds set forth in Table 1, or a pharmaceutically acceptable salt, ester, amide or prodrug thereof:

TABLE 1

| Comp'd No. | Structure |
|---|---|
| 1 | ![structure 1] |
| 2 | ![structure 2] |
| 3 | ![structure 3] |
| 4 | ![structure 4] |
| 5 | ![structure 5] |

TABLE 1-continued

| Comp'd No. | Structure |
|---|---|
| 6 | 4-chlorophenacyl thiocyanate |
| 7 | 4-acetamidophenacyl thiocyanate |
| 8 | 3-bromophenacyl thiocyanate |
| 9 | 3-methoxyphenacyl thiocyanate |
| 10 | 4-methoxyphenacyl thiocyanate |
| 11 | 4-(pyrrolidin-1-yl)phenacyl thiocyanate |
| 12 | 3,4-dimethoxyphenacyl thiocyanate |
| 13 | 4-(diethylamino)phenacyl thiocyanate |

TABLE 1-continued
| Comp'd No. | Structure |
|---|---|
| 14 | 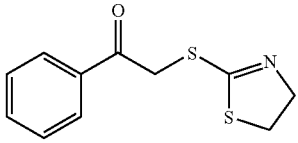 |
| 15 | 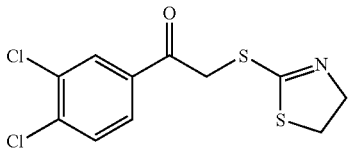 |
| 16 | 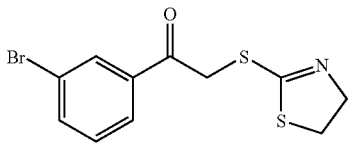 |
| 17 | 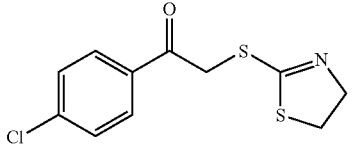 |
| 18 | 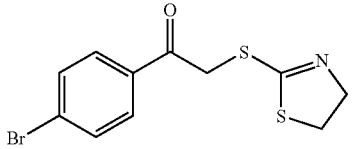 |
| 19 | 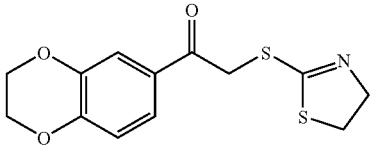 |
| 20 | 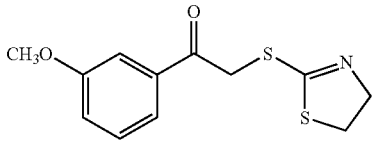 |
| 21 | 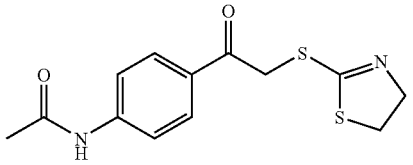 |
| 22 | 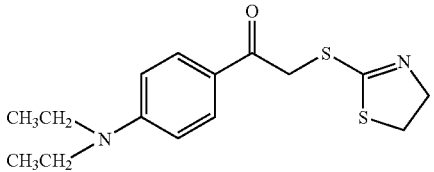 |

TABLE 1-continued

| Comp'd No. | Structure |
|---|---|
| 23 | 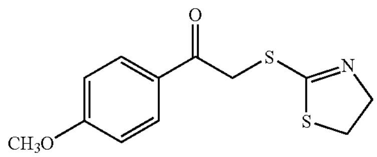 |
| 24 | 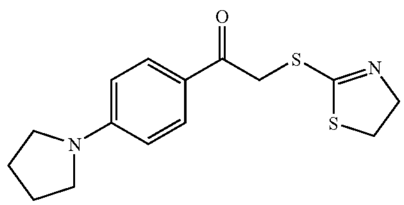 |
| 25 | 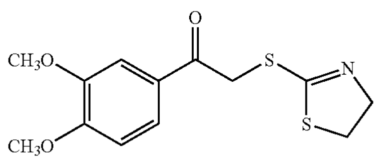 |
| 26 | 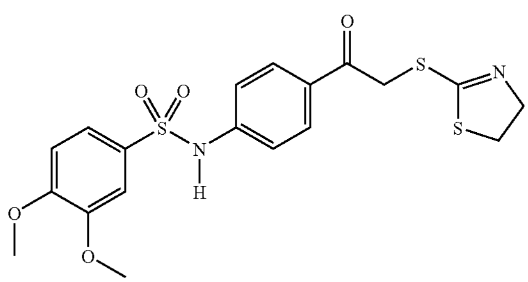 |
| 27 | 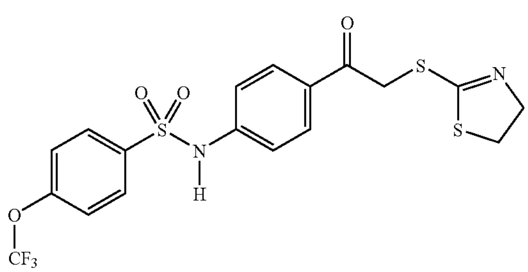 |
| 28 | 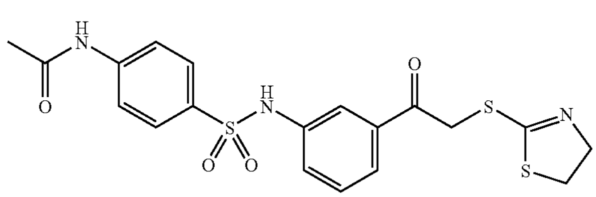 |
| 29 | 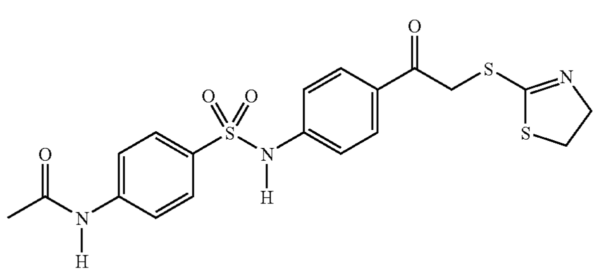 |

TABLE 1-continued
| Comp'd No. | Structure |
|---|---|
| 30 | 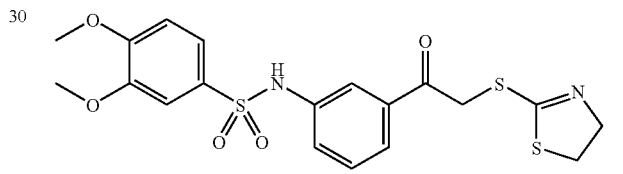 |
| 31 | 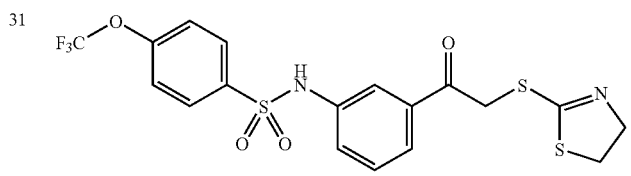 |
| 32 | 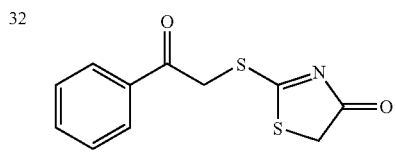 |
| 33 | 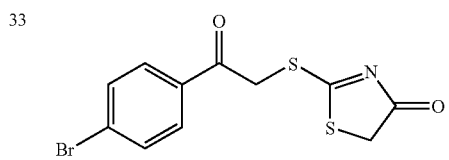 |
| 34 | 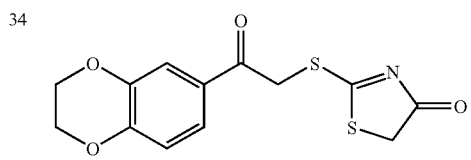 |
| 35 | 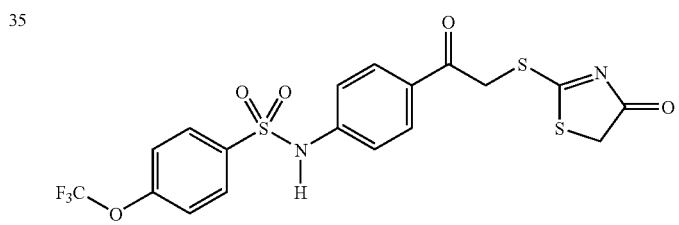 |
| 36 | 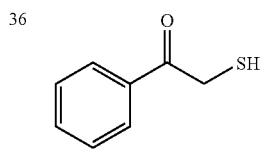 |
| 37 | 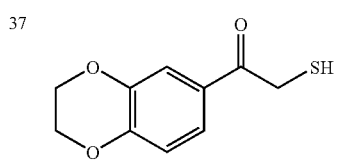 |

TABLE 1-continued
| Comp'd No. | Structure |
|---|---|
| 38 | 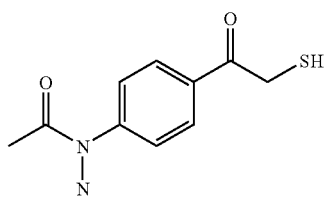 |
| 39 | 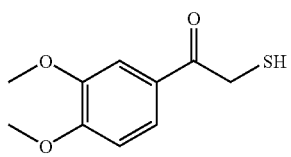 |
| 40 | 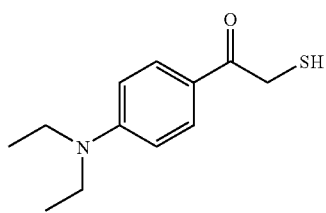 |
| 41 | 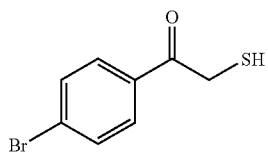 |
| 42 | 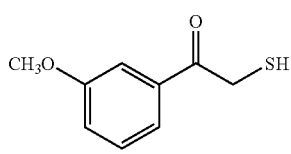 |
| 43 | 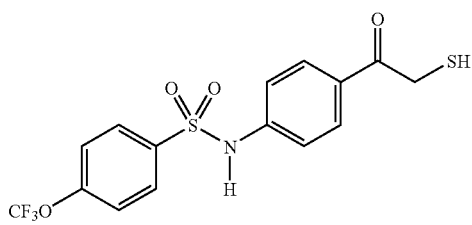 |
| 44 | 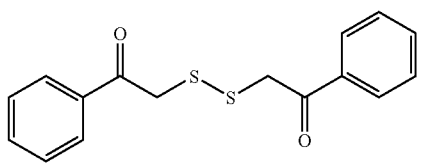 |

TABLE 1-continued

| Comp'd No. | Structure |
|---|---|
| 45 | 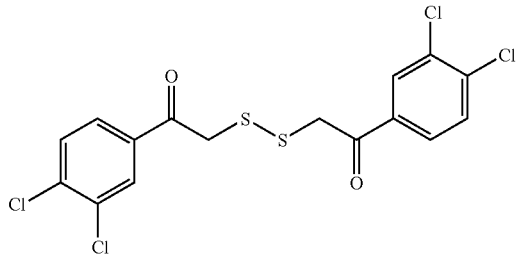 |
| 46 | 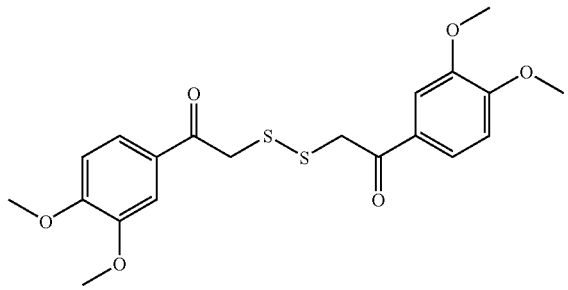 |
| 47 | 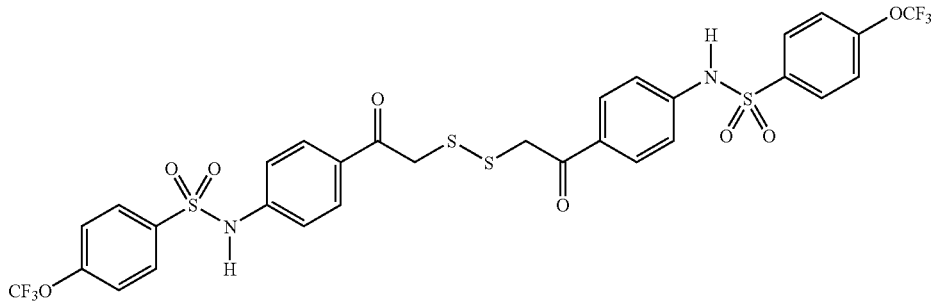 |
| 48 | 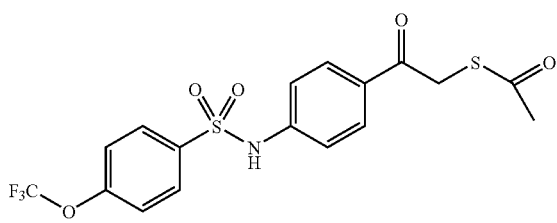 |

In another aspect, the present invention is directed to a compound of Formula I, II, or III, as defined herein, including those in Table 1, where the compound is capable of inhibiting the catalytic activity of hi stone deacetylase (HDAC).

Another aspect of the present invention are compounds containing at least one thiol in a protected form, which can be released to provide a SH group prior to or simultaneous to use. Thiol moieties are known to be unstable in the presence of air and are oxidized to the corresponding disulfide. Protected thiol groups are those that can be converted under mild conditions into free thiol groups without other undesired side reactions taking place. Suitable thiol protecting groups include but are not limited to trityl (Trt), allyloxycarbonyl (Alloc), 1-(4,4-dimethyl-2,6-dioxocyclohex-1-ylidene)ethyl (Dde), acetamidomethyl (Acm), t-butyl (tBu), or the like. Preferred thiol protecting groups include lower alkanoyl, e.g. acetyl. Free thiol, disulfides, and protected thiols are understood to be within the scope of this invention.

Another embodiment of the invention is compounds of Formula IV,

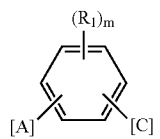

(IV)

or a pharmaceutically acceptable salt, amide, ester, or prodrug thereof, or a pharmaceutical composition comprising such compounds and a pharmaceutically acceptable carrier, diluent or excipient, wherein a) A is

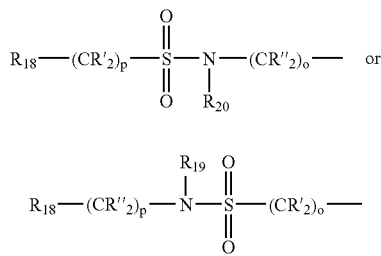

wherein $R_{18}$ is a lower alkyl, lower heteroalkyl, or five-, six-, seven-, or eight-membered carbocyclic or heterocyclic aliphatic ring, or a five-membered or six-membered heteroaryl ring or a six-membered aryl ring, each optionally substituted with one or more substituents selected from the group consisting of
  i) optionally substituted $C_1$-$C_8$ straight-chain, branched, or cyclic saturated or unsaturated alkyl;
  ii) an alkoxy of formula —$(X_1)_{n1}$—O—$X_2$, where
    $X_1$ is selected from the group consisting of lower alkylene, lower alkenylene, lower alkynylene, aryl, and heteroaryl;
    $X_2$ is selected from the group consisting of hydrogen, lower alkyl, lower perhaloalkyl, aryl, and heteroaryl; and
    n1 is 0, 1, 2 or 3;
  iii) halogen, partially halogenated alkyl, or perhaloalkyl;
  iv) cyano;
  v) nitro;
  vi) an amino of formula —$(X_3)_{n3}$—$NX_4X_5$, where
    $X_3$ is selected from the group consisting of lower alkylene, lower alkenylene, lower alkynylene, aryl, and heteroaryl;
    $X_4$ and $X_5$ are each independently selected from the group consisting of hydrogen, lower alkyl, aryl, and heteroaryl; or $X_4$ and $X_5$, taken together with the nitrogen to which they are attached, form a five-membered or six-membered heteroaromatic or heteroaliphatic ring; and
    n3 is 0 or 1;
  vii) a thioether or thiol of formula —$(X_6)_{n6}$—S—$X_7$, where
    $X_6$ is selected from the group consisting of lower alkylene, lower alkenylene, lower alkynylene, aryl, and heteroaryl;
    $X_7$ is selected from the group consisting of hydrogen, lower alkyl, perfluoroalkyl, aryl, and heteroaryl; and
    n6 is 0, 1, 2, or 3; and
  viii) an amide of formula —$(X_7)_{n7}$—NH—C(O)—$X_8$ or —$(X_9)_{n9}$—C(O)—NH—$X_{10}$
    $X_7$ and $X_9$ are each independently selected from the group consisting of lower alkylene, lower alkenylene, lower alkynylene, aryl, and heteroaryl;

$X_8$ is selected from the group consisting of hydrogen, lower alkyl, lower alkenyl, aryl, lower heteroalkyl, heteroaryl, hydroxy, alkoxy, and amide; and $X_{10}$ is selected from the group consisting of hydrogen, lower alkyl, lower alkenyl, aryl, lower heteroalkyl, and heteroaryl;

n7 and n9 are each independently is 0 or 1;

R' and R" are each independently selected from the group consisting of hydrogen and lower alkyl;

Wherein $R_{19}$ is H, $C_{1-5}$ alkyl, or $R_{19}$ taken together with $R^1$ forms a five-, six-, seven-, or eight-membered heterocyclic ring, o is 0, and the compound of formula IV has the following structure:

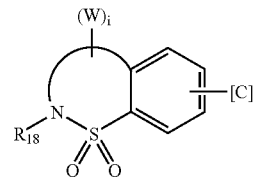

and W is independently selected from the group consisting of
  A) hydrogen;
  B) optionally substituted $C_1$-$C_8$ straight-chain, branched, or cyclic saturated or unsaturated alkyl;
  C) optionally substituted aryl;
  D) optionally substituted heterocyclyl;
  E) an alkoxy of formula —$(X_{13})_{n13}$—O—$X_{14}$, where
    $X_{13}$ is selected from the group consisting of lower alkylene, lower alkenylene, lower alkynylene, aryl, and heteroaryl;
    $X_{14}$ is selected from the group consisting of hydrogen, lower alkyl, lower perhaloalkyl, aryl, and heteroaryl; $n_{13}$=O, 1, 2, or 3; and
i is 0, 1, 2, 3, 4;
wherein $R_{20}$ is H, $C_{1-5}$ alkyl, or $R_{20}$ taken together with $R_{18}$ forms a five-, six-, seven-, or eight-membered heterocyclic ring, having the following structure:

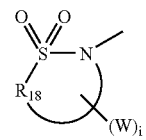

b) wherein each $R_1$ is each independently selected from the group consisting of
  i) hydrogen;
  ii) lower alkyl;
  iii) lower alkylene;
  iv) halogen, partially halogenated alkyl, or perhaloalkyl;
  v) an alkoxy or perhaloalkoxy;

c) wherein [C] is

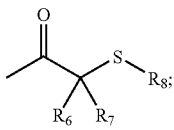

d) $R_8$ is selected from the group consisting of
  i) hydrogen;
  ii) optionally substituted $C_1$-$C_8$ straight-chain, branched, or cyclic saturated or unsaturated alkyl;
  iii) cyano;

iv) 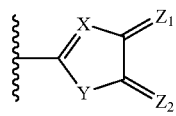

wherein
    X is selected from CH and nitrogen;
    Y is selected from the group consisting of $CH_2$, NH, oxygen and sulfur;
    $Z_1$ and $Z_2$ are each independently selected from the group consisting of null, oxygen, sulfur, and $CR_{11}R_{12}$,
      wherein $R_{11}$ and $R_{12}$ are each independently selected from the group consisting of hydrogen, lower alkyl, lower alkoxy, aryl, aryloxy, $NH_2$, halogen, perhaloalkyl, and hydroxy; and v) 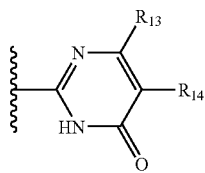

wherein $R_{13}$ and $R_{14}$ are each independently selected from the group consisting of hydrogen, lower alkyl, lower alkoxy, aryl, aryloxy, $NH_2$, halogen, perhaloalkyl, and hydroxy;
  vi) optionally substituted acyl of the formula $-OC(O)R_E$, wherein $HOC(O)R_E$ is a pharmaceutically acceptable acid
  vii) or $R_8$ is equivalent to the balance of Formula IV to form a disulfide dimer;

e) $R_6$ and $R_7$ are each independently selected from the group consisting of hydrogen and lower alkyl.

In another aspect are compounds having structural Formula IV wherein $R_{19}$ and $R_{20}$ are each independently H or $C_{1-5}$ alkyl, and o and p are 0.

In another aspect are compounds having structural Formula IV wherein $R_{18}$ is optionally substituted phenyl.

In another aspect are compounds having structural Formula IV wherein said $R_8$ forms a pharmaceutically acceptable acid upon thioester hydrolysis. Representaive acids include N,N-diethylglycine; 4-ethylpiperazinoacetic acid; ethyl 2-methoxy-2-phenylacetic acid; N,N-dimethylglycine; (nitrophenoxysulfonyl)benzoic acid, acetic acid, maleic acid, fumaric acid, benzoic acid, tartraric acid, glutamic acid, aspartic acid, proline, D-amino acids, butyric acid, palmitic acid, stearic acid, oleaic acid, pipecolic acid, phosphonic acid, phosphoric acid, pivalate(trimethylacetic acid), succinic acid, cinnamic acid, anthranilic acid, salicylic acid, lactic acid, and, pyruvic acids.

In another aspect are compounds having structural Formulae V or VI, VII, or VIII:

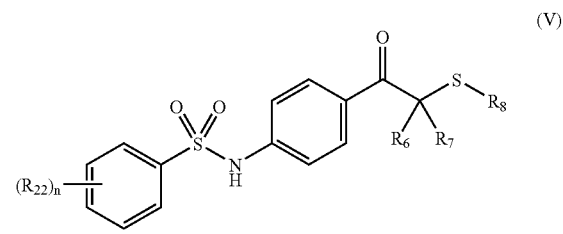

(V)

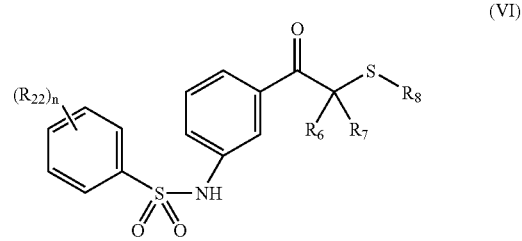

(VI)

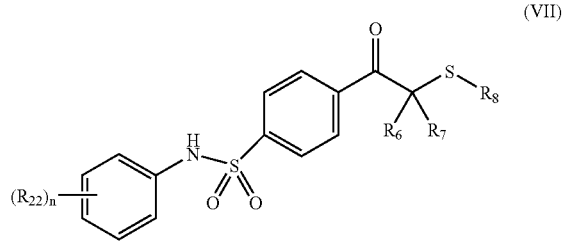

(VII)

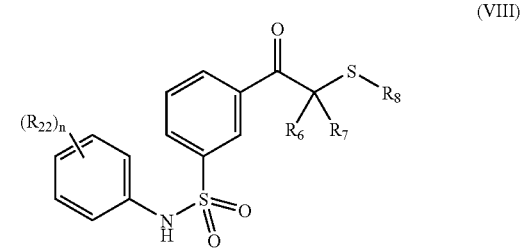

(VIII)

wherein
a) $R_6$ and $R_7$ are each independently selected from the group consisting of hydrogen and lower alkyl;
b) $R_8$ is selected from the group consisting of H, acyl, and heterocyclyl;
c) $R_{22}$ is selected from the group consisting of $C_{1-5}$ alkyl, $C_{1-5}$ perhaloalkyl, $C_{1-5}$ alkoxy, $C_{1-5}$ perhaloalkyl alkoxy, and N-alkylamido;
d) n=0, 1, 2, 3.

In another aspect are compounds having structural Formula:

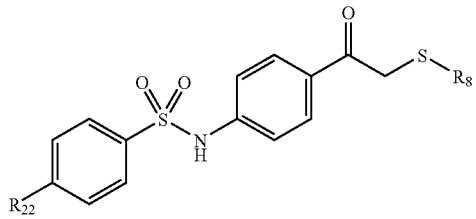

and wherein $R_{22}$ is $C_{1-5}$ perfluoroalkyl and $R_8$ is a thiol protecting group as described herein.

In another aspect are compounds or compositions comprising compounds capable of inhibiting the catalytic activity of histone deacetylase (HDAC).

In some aspects of the invention, the disease to be treated by the methods of the present invention may be cancer. In some embodiments, but without limitation, the term cancer refers to and is selected from disorders such as colon cancer, breast cancer, ovarian cancer, lung cancer and prostrate cancer, tumor invasion, tumor growth, tumor metastasis, and cancers of the oral cavity and pharynx (lip, tongue, mouth, pharynx), esophagus, stomach, small intestine, large intestine, rectum, liver and biliary passages, pancreas, larynx, bone, connective tissue, skin, cervix uteri, corpus endometrium, testis, bladder, kidney and other urinary tissues, eye, brain and central nervous system, thyroid and endocrine gland. The term "cancer" also encompasses Hodgkin's disease, non-Hodgkin's lymphomas, multiple myeloma and hematopoietic malignancies including leukemias (Chronic Lymphocytic Leukemia) and lymphomas including lymphocytic, granulocytic and monocytic.

Additional types of cancers which may be treated using the compounds and methods described herein include: adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, cancer of the larynx, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor In some aspects of the invention, the disease to be treated by the methods of the present invention may be a neurological or polyglutamine-repeat disorder. In some embodiments, but without limitation, the polyglutamine-repeat disorder is selected from Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA) and Dentatorubral pallidolusyian atrophy (DRPLA).

In some aspects of the invention, the disease to be treated by the methods of the present invention may be an anemias or thalassemia (such as Sickle Cell Disease (SCD). In some embodiments, but without limitation, the thalassemia is Sickle Cell Disease (SCD).

In some aspects of the invention, the disease to be treated by the methods of the present invention may be an inflammatory condition. In some embodiments, but without limitation, the inflammatory condition is selected from Rheumatoid Arthritis (RA), Inflammatory Bowel Disease (IBD), ulcerative colitis and psoriasis.

In some aspects of the invention, the disease to be treated by the methods of the present invention may be an autoimmune disease. In some embodiments, but without limitation, the autoimmune disease is selected from Systemic Lupus Erythromatosus (SLE) and Multiple Sclerosis (MS).

In some aspects of the invention, the disease to be treated by the methods of the present invention may be a cardiovascular condition. In some embodiments, but without limitation, the cardiovascular condition is selected from cardiac hypertrophy and heart failure.

The terms "therapy" or "treating" as used herein refer to (1) reducing the rate of progress of a disease, or, in case of cancer reducing the size of the tumor; (2) inhibiting to some extent further progress of the disease, which in case of cancer may mean slowing to some extent, or preferably stopping, tumor metastasis or tumor growth; and/or, (3) relieving to some extent (or, preferably, eliminating) one or more symptoms associated with the disease. Thus, the term "therapeutically effective amount" as used herein refers to that amount of the compound being administered which will provide therapy or affect treatment.

In some aspects of the invention, the compounds of the present invention are also anti-tumor compounds and/or inhibit the growth of a tumor, i.e., they are tumor-growth-inhibiting compounds. The terms "anti-tumor" and "tumor-growth-inhibiting," when modifying the term "compound," and the terms "inhibiting" and "reducing", when modifying the terms "compound" and/or "tumor," mean that the presence of the subject compound is correlated with at least the slowing of the rate of growth of the tumor. More preferably, the terms "anti-tumor," "tumor-growth-inhibiting," "inhibiting," and "reducing" refer to a correlation between the presence of the subject compound and at least the temporary cessation of tumor growth. The terms "anti-tumor," "tumor-growth-inhibiting," "inhibiting," and "reducing" also refer to, a correlation between the presence of the subject compound and at least the temporary reduction in the mass of the tumor.

The term "function" refers to the cellular role of HDAC. The term "catalytic activity", in the context of the invention, defines the rate at which HDAC deacetylates a substrate. Catalytic activity can be measured, for example, by determining the amount of a substrate converted to a product as a function of time. Deacetylation of a substrate occurs at the active-site of HDAC. The active-site is normally a cavity in which the substrate binds to HDAC and is deacetylated.

The term "substrate" as used herein refers to a molecule deacetylated by HDAC. The substrate is preferably a peptide and more preferably a protein. In some embodiments, the protein is a histone, whereas in other embodiments, the protein is not a histone.

The term "activates" refers to increasing the cellular function of HDAC. The term "inhibit" refers to decreasing the cellular function of HDAC. HDAC function is preferably the interaction with a natural binding partner and most preferably catalytic activity.

The term "modulates" refers to altering the function of HDAC by increasing or decreasing the probability that a complex forms between HDAC and a natural binding partner. A modulator may increase the probability that such a complex forms between HDAC and the natural binding partner, or may increase or decrease the probability that a complex forms between HDAC and the natural binding partner depending on the concentration of the compound exposed to HDAC, or may decrease the probability that a complex forms between HDAC and the natural binding partner. A modulator may activate the catalytic activity of HDAC, or may activate or inhibit the catalytic activity of HDAC depending on the concentration of the compound exposed to HDAC, or may inhibit the catalytic activity of HDAC.

The term "complex" refers to an assembly of at least two molecules bound to one another. The term "natural binding partner" refers to polypeptides that bind to HDAC in cells. A change in the interaction between HDAC and a natural binding partner can manifest itself as an increased or decreased probability that the interaction forms, or an increased or decreased concentration of HDAC/natural binding partner complex.

The term "contacting" as used herein refers to mixing a solution comprising a compound of the invention with a liquid medium bathing the cells of the methods. The solution comprising the compound may also comprise another component, such as dimethylsulfoxide (DMSO), which facilitates the uptake of the compound or compounds into the cells of the methods. The solution comprising the compound of the invention may be added to the medium bathing the cells by utilizing a delivery apparatus, such as a pipet-based device or syringe-based device.

The term "monitoring" refers to observing the effect of adding the compound to the cells of the method. The effect can be manifested in a change in cell phenotype, cell proliferation, HDAC catalytic activity, substrate protein acetylation levels, gene expression changes, or in the interaction between HDAC and a natural binding partner.

The term "effect" describes a change or an absence of a change in cell phenotype or cell proliferation. "Effect" can also describe a change or an absence of a change in the catalytic activity of HDAC. "Effect" can also describe a change or an absence of a change in an interaction between HDAC and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

A. Pharmaceutical Compositions

The present invention also relates to a pharmaceutical composition comprising
  a) a compound of the invention, or a pharmaceutically acceptable salt, solvate, amide, ester, or prodrug thereof, as described herein; and
  b) a pharmaceutically acceptable carrier, diluent, or excipient, or a combination thereof.

The term "pharmaceutical composition" refers to a mixture of a compound of the invention with other chemical components, such as carriers, diluents or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to relatively nontoxic chemical compounds or agents. Such carriers may facilitate the incorporation of a compound into cells or tissues. For example, human serum albumin (HSA) is a commonly utilized carrier as it facilitates the uptake of many organic compounds into the cells or tissues of an organism.

The term "diluent" refers to chemical compounds that are used to dilute the compound of interest prior to delivery. Diluents can also be used to stabilize compounds because they can provide a more stable environment. Salts dissolved in buffered solutions (providing pH control) are utilized as diluents in the art. One commonly used buffered solution is phosphate buffered saline. It is a buffer found naturally in the blood system. Since buffer salts can control the pH of a solution at low concentrations, a buffered diluent rarely modifies the biological activity of a compound.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," 20th ed. Edited by Alfonso Gennaro, 2000.

1) Routes of Administration

Suitable routes of administration may, for example, include oral, rectal, transmucosal, pulmonary, ophthalmic or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ.

2) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or compression processes.

Pharmaceutical compositions for use in accordance with the present invention thus may be formulated in conventional manner using one or more pharmaceutically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For intravenous injections, the agents of the invention may be formulated in aqueous solutions, preferably in pharmaceutically compatible buffers such as Hanks's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with pharmaceutically compatible buffers or excipients. Such excipients are generally known in the art.

For oral administration, the compounds can be formulated readily by combining the active compounds with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethy I cellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG-40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

EXAMPLES

The examples below are non-limiting and are merely representative of various aspects of the invention.

Example 1

General Procedure for the Synthesis of Thiocyanates

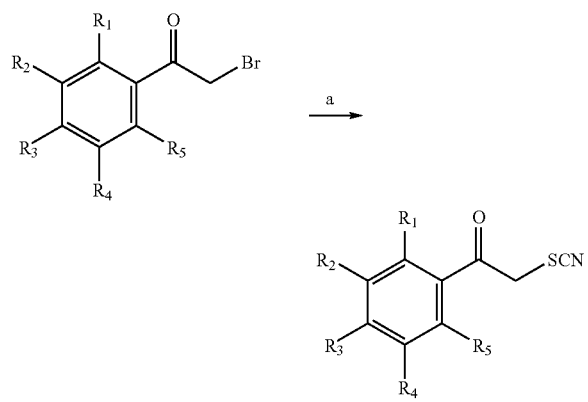

Reagents: (a) NaSCN, EtOH

Sodium thiocyanide (1 eq.) is dissolved in ethanol (9 mL) before the alpha-bromo ketone (1 eq.) is added as a solid. The resulting solution is then allowed to stir at room temperature for 10 minutes. The volatiles are removed under a stream of nitrogen and the resulting residue is taken up in ethyl acetate before being extracted with water. The organic fraction is dried over $Na_2SO_4$ and evaporated to leave an oil which is crystallized upon standing. The product is purified by radial chromatography and recrystallized from EtOAc/hexanes.

This general procedure was utilized for the preparation of Compounds 1-13, and is specifically exemplified for Compound 1, below:

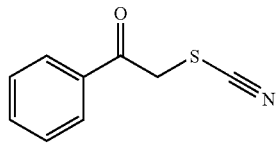

Compound 1

Compound 1: Synthesis of 1-Phenyl-2-thiocyanato-ethanone:

Sodium thiocyanide (200 mg, 2.47 mmol) was dissolved in ethanol (9 mL) before 1-bromoacetophenone (481 mg, 2.42 mmol) was added as a solid. The resulting tan solution was then allowed to stir at room temperature for 10 minutes. The volatiles were removed under a stream of nitrogen and the resulting residue was taken up in ethyl acetate before being extracted with water. The organic fraction was dried over $Na_2SO_4$ and evaporated to leave an oil which crystallized upon standing. The product, Compound 1 was purified by radial chromatography and recrystallized from EtOAc/hexanes (400 mg, 2.26 mmol, 93%). It had $^1$H-NMR: ($CDCl_3$) 7.94 (dd, 2H), 7.66 (m, 1H), 7.56 (m, 2H), 4.75 (s, 2H) ppm. It had LCMS (ES+): 91 $[M-C_2NOS]^+$ m/e.

Compounds 2-13 were similarly prepared.

Example 2

General Procedure for the Synthesis of Thiazolines

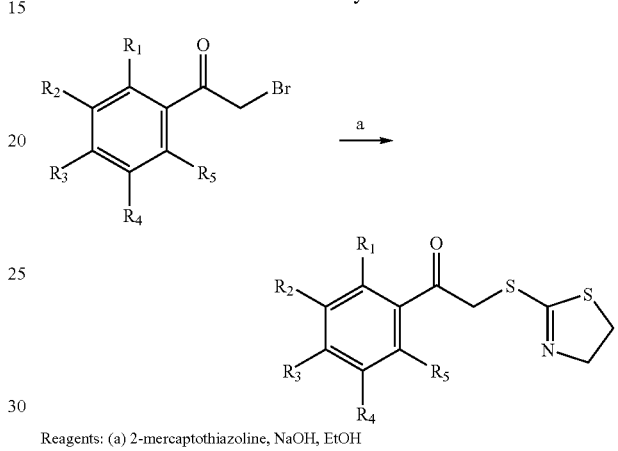

Reagents: (a) 2-mercaptothiazoline, NaOH, EtOH

2-Mercaptothiazoline (1 eq.) is suspended in ethanol (7 mL) before NaOH(1.8 mL, 2 M) is added affording a clear solution. The alpha-bromo ketone compound (1 eq.) is then added as a solid and the resulting solution is allowed to stir at 40° C. for 3 hours. The volatiles are then removed under a stream of nitrogen before water and EtOAc are added for extraction. The organic layer is dried over $Na_2SO_4$ and evaporated to leave a dark residue which is purified by radial chromatography. The product is recrystallized from EtOAc/hexanes.

This general procedure was utilized for the preparation of Compounds 14-31, and is specifically exemplified for Compound 14, with analytical data in support of characterization of Compounds 26, 27, 28 and 29, below:

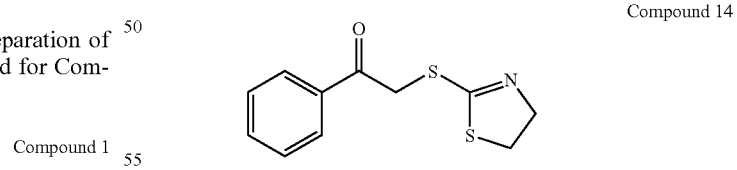

Compound 14

Compound 14: Synthesis of 2-(4,5-Dihydro-thiazol-2-ylsulfanyl)-1-phenyl-ethanone:

2-Mercaptothiazoline (300 mg, 2.5 mmol) was suspended in ethanol (7 mL) before NaOH(1.8 ml, 2 M) was added affording a clear solution. 1-Bromoacetophenone (491 mg, 2.47 mmol) was then added as a solid and the resulting red solution was allowed to stir at 40° C. for 3 hours. The volatiles were then removed under a stream of nitrogen before water and EtOAc were added for extraction. The organic layer was dried over $Na_2SO_4$ and evaporated to leave a dark residue which was purified by radial chromatography. The purified product, Compound 14, was recrystallized from EtOAc/hexanes (500 mg, 84%). It had $^1$H-NMR: (CDCl$_3$) 8.01 (m, 2H), 7.60 (m, 1H), 7.48 (m, 2H), 4.69 (s, 2H), 4.18 (t, 2H), 3.43 (t, 2H) ppm. It had LCMS (ES+): 238 [MH]$^+$ m/e.

Compound 26

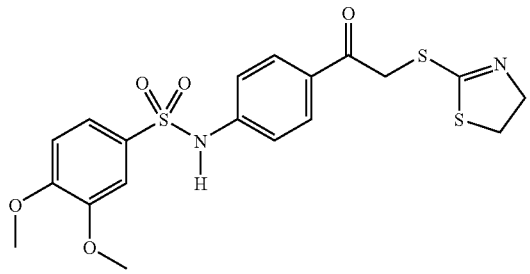

Compound 26: Characterization of N-{4-[2-(4,5-Dihydro-thiazol-2-ylsulfanyl)-acetyl]-phenyl}-3,4-dimethoxy-benzenesulfonamide $^1$H-NMR: (DMSO-d$_6$) 10.75 (s, 1H), 7.88 (d, 2H), 7.50 (d, 1H), 7.31 (d, 1H), 7.23 (d, 2H), 7.08 (d, 1H), 4.70 (s, 2H), 4.04 (t, 2H), 3.79 (s, 3H), 3.77 (s, 3H), 3.43 (t, 2H)ppm. It had LC-MS (ES+): 453 [M]$^+$ m/e.

Compound 27

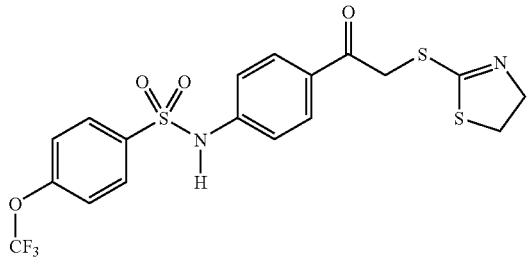

Compound 27: Characterization of N-{4-[2-(4,5-Dihydro-thiazol-2-ylsulfanyl)-acetyl]-phenyl}-4-trifluoromethoxy-benzenesulfonamide $^1$H-NMR: (CDCl$_3$) 7.91 (d, 2H), 7.88 (d, 2H), 7.29 (d, 2H), 7.17 (d, 2H), 6.71 (bs, 1H), 4.59 (s, 2H), 4.16 (t, 2H), 3.43 (t, 2H) ppm. It had LC-MS (ES+): 477 [M]$^+$ m/e.

Compound 28

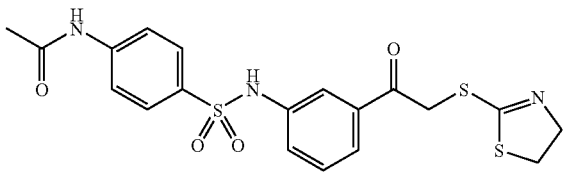

Compound 28: Characterization of N-(4-{3-[2-(4,5-Dihydro-thiazol-2-ylsulfanyl)-acetyl]phenylsulfamoyl}-phenyl)-acetamide $^1$H-NMR: (DMSO-d$_6$) 10.40 (bs, 1H), 10.30 (bs, 1H), 7.70 (m, 6H), 7.30 (m, 2H), 4.70 (s, 1H), 4.1 (t, 2H), 3.50 (t, 2H), 2.00 (s, 3H) ppm. It had LC-MS (ES+): 450 [M]$^+$ m/e.

Compound 29

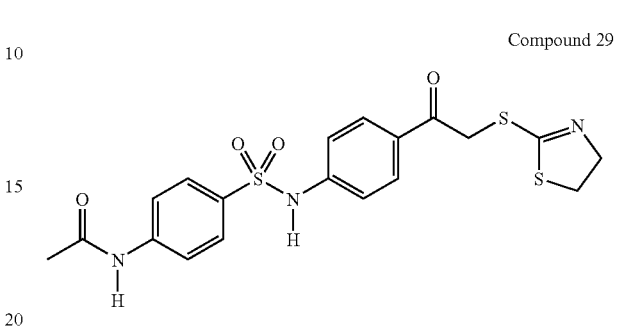

Compound 29: Characterization of N-(4-{4-[2(4,5-Dihydro-thiazol-2-ylsulfanyl)-acetyl]-phenylsulfamoyl}-phenyl)-acetamide $^1$H-NMR: (DMSO-d$_6$) 10.80 (bs, 1H), 10.30 (bs, 1H), 7.86 (d, 2H), 7.76 (m, 4H), 7.19 (d, 2H), 4.69 (s, 2H), 4.03 (t, 2H), 3.42 (t, 2H), 2.05 (s, 3H) ppm. It had LC-MS (ES+): 450 [M]$^+$ m/e.

Compounds 15-25, 30 and 31 were similarly prepared.

Example 3

General Procedure for the Synthesis of Thiazolinones

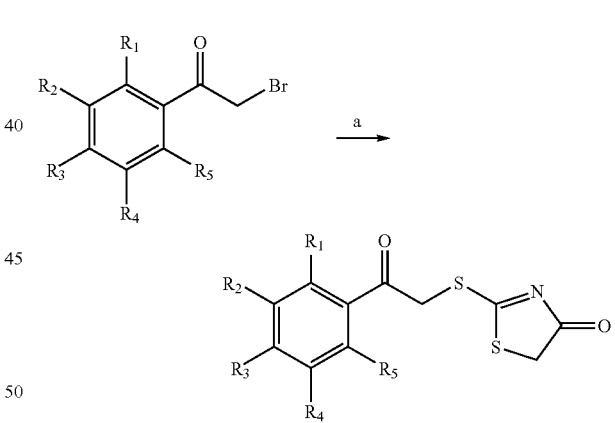

Reagents: (a) EtOH, NaOH, Rhodanine

Rhodanine (1.0 eq.) is dissolved in EtOH (2 mL) and 2 M NaOH (0.275 mL) with vigorous stirring. Once the Rhodanine is completely dissolved, the alpha-bromo ketone compound (1 eq.) is added with constant stirring. The reaction is mixed overnight at 40° C. After 18 hrs the reaction is removed from the heat and left stirring at room temp for 48 hrs. The resulting reaction mixture is then diluted with water (5 mL) and extracted with dichloromethane (3×5 ml). The organic layer is dried over Na$_2$SO$_4$ and then evaporated to yield an oil. The oil is purified by chromatotron using a 50/50 mixture of ethyl acetate in hexanes as the mobile phase. The purified product is then recrystallized in hexanes to complete its purification.

This general procedure was utilized for the preparation of Compounds 32-35, and is specifically exemplified for Compounds 34, below:

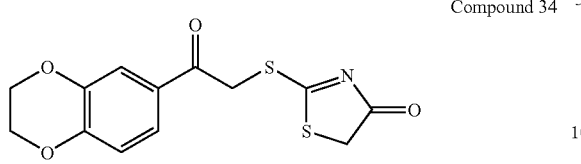

Compound 34

Compound 34: Synthesis of 2-[2-(2,3-Dihydro-benzo[1,4]dioxin-6-yl)-2-oxo-ethylsulfanyl]-thiazol-4-one:

Rhodanine (0.052 g, 0.388 mmol, 1.0 eq.) was dissolved in EtOH (2 ml) and 2 M NaOH (0.275 ml, 0.550 mmol, 1.42 eq.) with vigorous stirring. Once the Rhodanine was completely dissolved, 6-Chloroacetyl-1,4-benzodioxane (0.080 g, 0.380 mmol, 0.98 eq.) was added with constant stirring. (It should be noted that α-chloro ketones were used when the corresponding α-bromo ketones were not available.) The reaction was mixed overnight at 40° C. After 18 hrs the reaction was removed from the heat and left stirring at room temp for 48 hrs. The resulting reaction mixture was then diluted with water (5 ml) and extracted with dichloromethane (3×5 ml). The organic layer was dried over $Na_2SO_4$ and then evaporated to yield an oil. The oil was purified by chromatotron using a 50/50 mixture of ethyl acetate in hexanes as the mobile phase. The purified product, Compound 34, was then recrystallized in hexanes to complete its purification (20 mg, 0.0646 mmol, 17%). The product was characterized by $^1$H-NMR: ($CDCl_3$) 7.55 (q, 2H), 6.93 (d, 1H), 4.93 (s, 2H), 4.31 (m, 4H), 4.02 (s, 2H) ppm. In addition LCMS [ES+] analysis yielded a single peak, 310 [M]$^+$ m/e.

Compounds 32, 33 and 35 were similarly prepared.

Example 4

General Procedure for the Synthesis of Mercaptans and Disulfides

Schemes 1a illustrates the general synthesis of disulfide embodiments of the present invention.

Scheme 1a

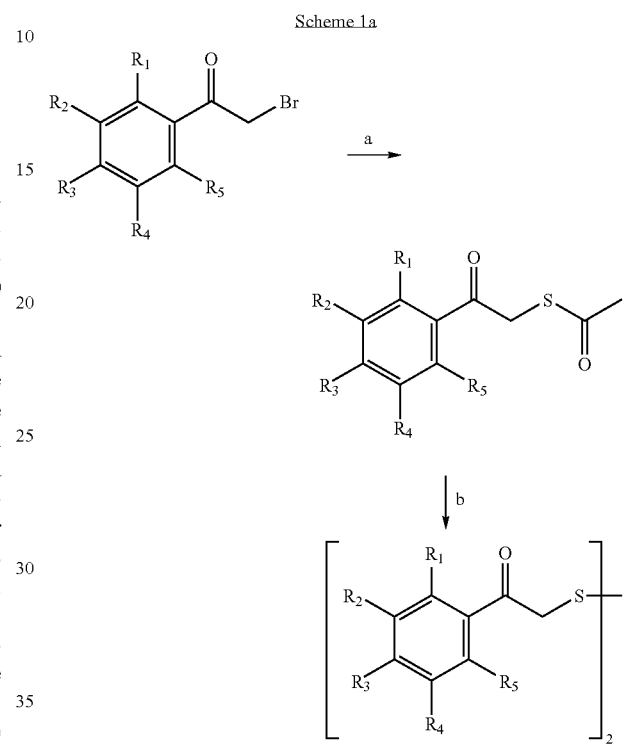

Reagents: (a) KSC(O)CH$_3$, MeOH; (b) NaOH, MeOH

Scheme 1b depicts an alternative general scheme for the synthesis of thiol (mercaptan) and disulfide embodiments of the present invention Scheme 1b

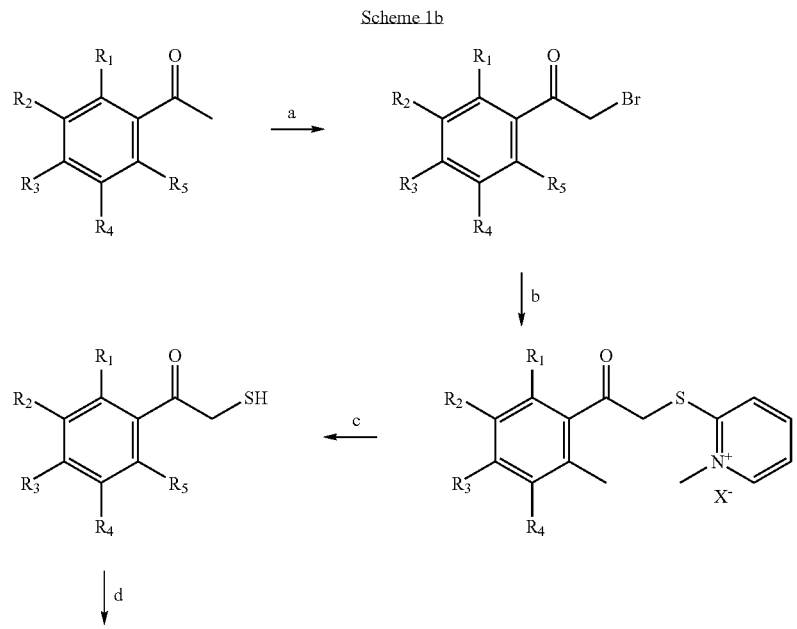

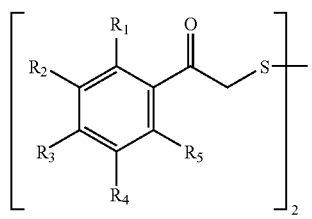
Reagents: (a) PPT, THF;
(b) N-methyl 2-thiopyrodine, EtOH;
(c) NaOH, water;
(d) MeOH, water.
Scheme 1c depicts the synthesis of Compound 47, and is exemplary of the general applicability of scheme 1a and 1b to specific alpha-thio ketone and disulfide molecular embodiments of the invention.
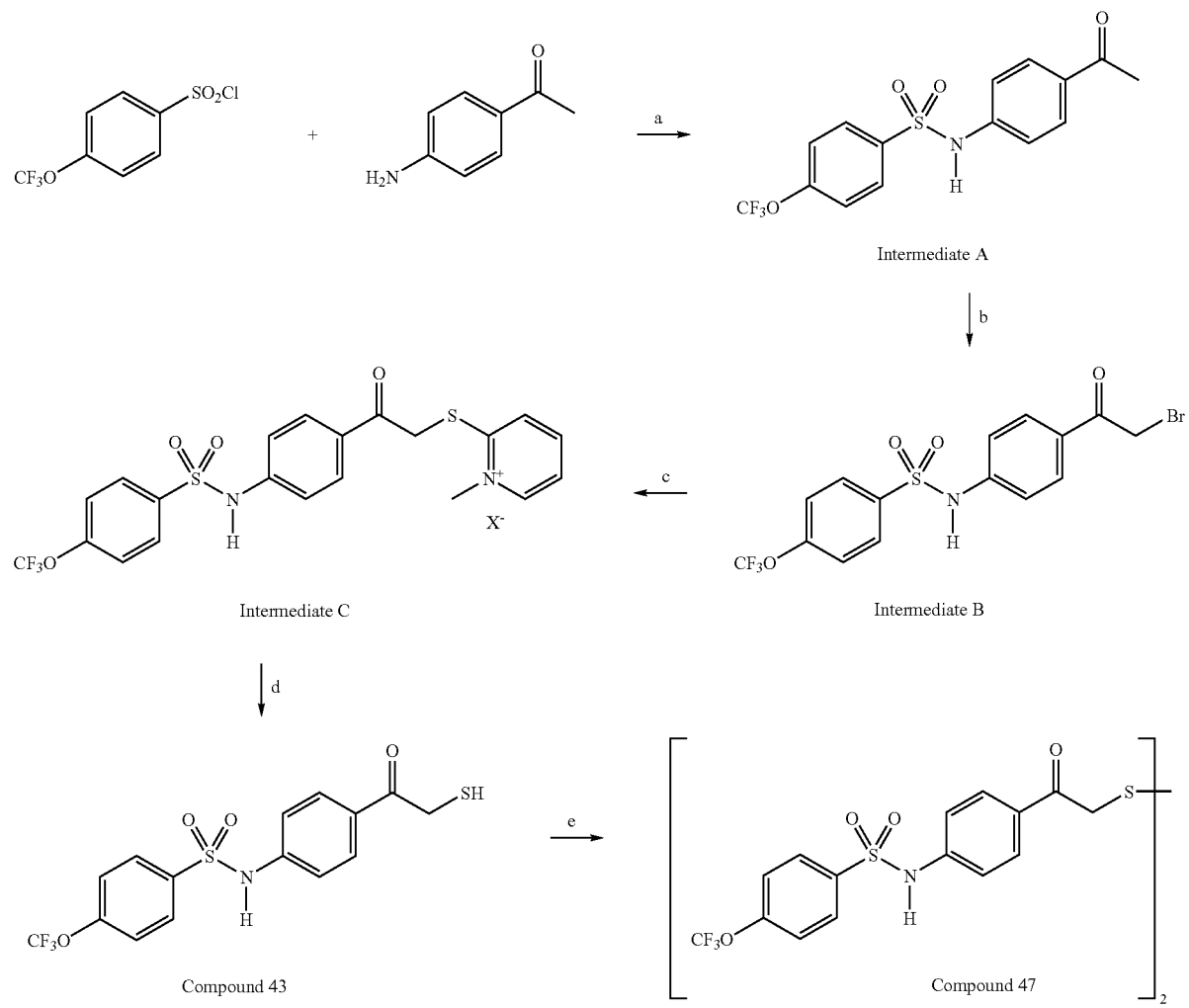
Reagents: (a) pyridine, THF;
(b) PTT, THF;
(c) N-methyl 2-thiopyrodine, EtOH;
(d) NaOH, water;
(e) MeOH, water.

Compound 47: Synthesis of Thioacetic acid S-{2-oxo-2-[4-(4-trifluoromethoxy-benzenesulfonylamino)-phenyl]-ethyl}disulfide

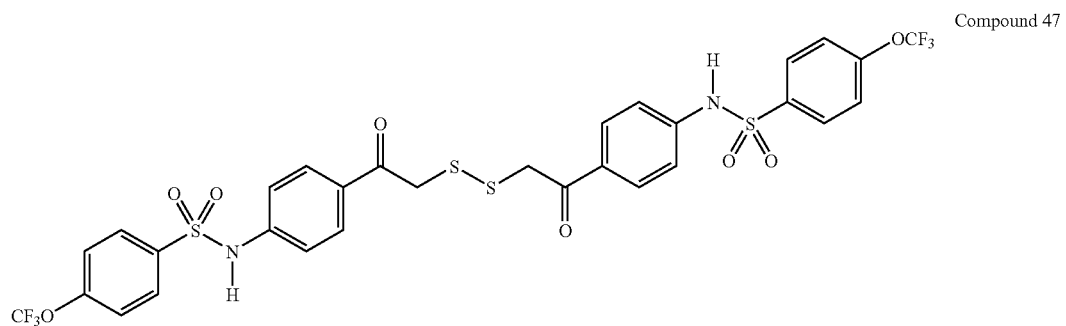
Compound 47

Step 1: Synthesis of Intermediate A

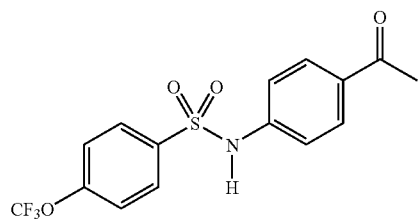
Intermediate A

Intermediate A: Synthesis of N-(4-Acetyl-phenyl)-4-trifluoromethoxy-benzenesulfonamide 4'-Amino acetophenone (0.375 g, 2.78 mmol) was dissolved in THF (5 ml) before pyridine (0.674 ml, 8.34 mmol) was added, leaving a yellow solution. 4-trifluoromethoxy benzenesulfonylchloride (0.871 g, 3.34 mmol) was then added dropwise with stirring. After removal of THF and pyridine, the desired sulfonamide (0.848 g, 2.36 mmol, 85%) was recrystallized from ethyl acetate and hexanes. $^1$H-NMR: (400 MHz, CDCl$_3$) 7.89 (m, 4H), 7.29 (d, 1H), 7.16 (d, 2H), 6.88 (s, 1H), 2.55 (s, 3H). LC-MS (ES+): 360 [MH]$^+$ m/e.

Step 2: Synthesis of Intermediate B

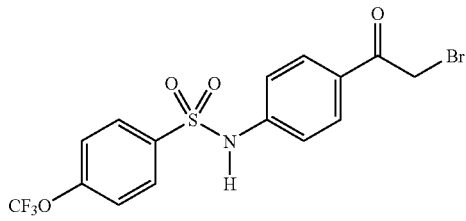
Intermediate B

Intermediate B: Synthesis of N-[4-(2-Bromo-acetyl)-phenyl]-4-trifluoromethoxy-benzenesulfonamide Intermediate A (0.32 g, 0.868 mmol) was dissolved in THF (9 ml), and phenyltrimethylammonium tribromide (PTT) (0.368 g, 0.868 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over Na$_2$SO$_4$ and evaporation leaves a white crystalline solid (90% desired mono-brominated material by LC-MS, 5% starting material, 5% dibrominated) suitable for the next step. LC-MS (ES—): 436, 438 m/e.

Step 3: Synthesis of Intermediate C

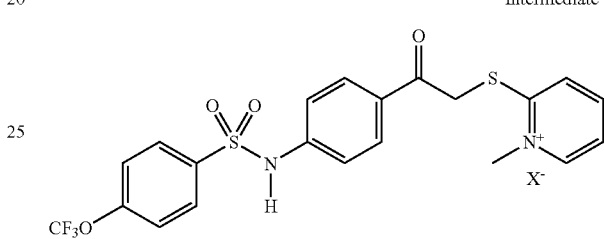
Intermediate C

Intermediate C: Synthesis of 1-Methyl-2-{2-oxo-2-[4-(4-trifluoromethoxybenzene-sulphonylamino)phenyl]ethylsulfanyl}-pyridinium bromide Intermediate B (0.141 g crude material, 0.322 mmol) was dissolved in ethanol (2 ml) before N-methyl thiopyridone (0.040 g, 0.322 mmol) was added as a solid. The resulting yellow solution was then heated to reflux overnight. Evaporation of the volatiles leaves a residue (75% by NMR, 0.116 g, 0.240 mmol) suitable for the next step, however, the product may be recrystallized from ethanol if desired. $^1$H-NMR: (400 MHz, DMSO-d$_6$) 11.21 (s, 1H), 8.90 (d, 1H), 8.18 (t, 1H), 8.03 (m, 5H), 7.90 (t, 1H), 7.80 (d, 2H), 7.15 (d, 2H), 5.33 (s, 2H), 4.24 (s, 3H). LC-MS (ES+): 483 [M]$^+$ m/e.

Steps 4 and 5: Synthesis of Compound 43 and Compound 47

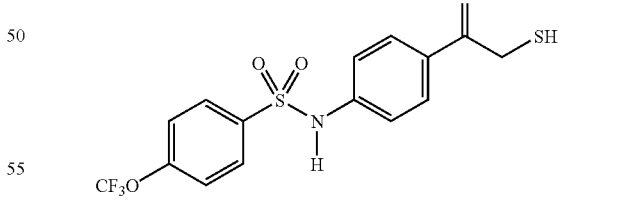
Compound 43

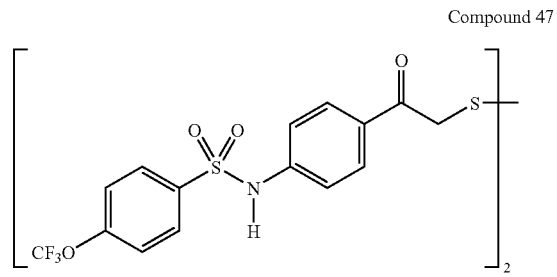
Compound 47

Compound 43 and Compound 47: Synthesis of N-[4-(2-Mercapto-acetyl)-phenyl]-4-trifluoromethoxy-benzenesulfonamide (43) and corresponding disulfide (47) Intermediate C (4.35 g, 7.72 mmol) was suspended in water (1.7 1) before 2 M NaOH (7.25 ml) was added. Solid NaOH (1 g) was then added, and the resulting mixture was then heated to reflux overnight, producing a red solution. The solution was then acidified to a pH of 1 and extracted with ethyl acetate. Drying over $Na_2SO_4$ and evaporation leaves a red oil. Throughout the work-up, the alpha-mercapto ketone readily oxidizes to the corresponding disulfide (47), which was purified by preparative HPLC (0.582 g, 0.75 mmol, 10%). $^1$H-NMR: (400 MHz, DMSO-$d_6$) 11.09 (bs, 2H), 7.97 (d, 4H), 7.85 (d, 4H), 7.57 (d, 4H), 7.22 (d, 4H), 4.29 (s, 4H). LC-MS (ES+): 781 [MH]$^+$ m/e.

Alpha thioketones Compounds 36-42 and disulfide Compounds 44-46 were similarly prepared.

Analytical data is support of the characterization of Compound 36-41 and Compounds 44-46 are presented below:

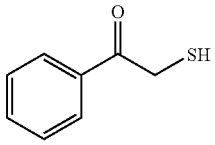

Compound 36

Compound 36: Characterization of 2-Mercapto-1-phenyl-ethanone
$^1$H-NMR: (400 MHz, CDCl$_3$) 7.99 (d, 2H), 7.61 (m, 1H), 7.51 (m, 2H), 3.97 (d, 2H), 2.14 (t, 1H). LC-MS (ES+): 153 [MH]$^+$ m/e.

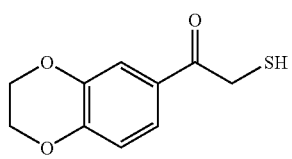

Compound 37

Compound 37: Characterization of 1-(2,3-Dihydro-benzo[1,4]dioxin-6-yl)-2-mercapto-ethanone
$^1$H-NMR: (400 MHz, CDCl$_3$) 7.50 (m, 2H), 6.93 (dd, 1H), 4.31 (m, 4H), 3.88 (d, 2H), 2.13 (t, 1H). LC-MS (ES+): 211 [MH]$^+$ m/e.

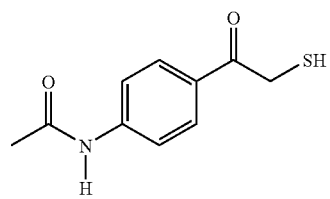

Compound 38

Compound 38: Characterization of N-[4-(2-Mercapto-acetyl)-phenyl]-acetamide
$^1$H-NMR: (400 MHz, DMSO-$d_6$) 10.32 (bs, 1H), 7.95 (d, 2H), 7.72 (d, 2H), 4.02 (d, 2H), 2.84 (t, 1H) 2.09 (s, 3H). LC-MS (ES+): 210 [MH]$^+$ m/e

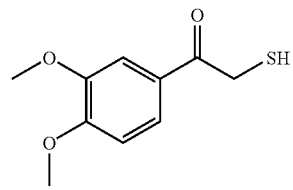

Compound 39

Compound 39: Characteriation of 1-(3,4-Dimethoxy-phenyl)-2-mercapto-ethanone
$^1$H-NMR: (400 MHz, CDCl$_3$) 7.56 (m, 2H), 6.91 (d, 1H), 3.96 (s, 3H), 3.95 (s, 3H), 3.92 (d, 2H), 2.15 (t, 1H). LC-MS (ES+): 213 [MH]$^+$ m/e.

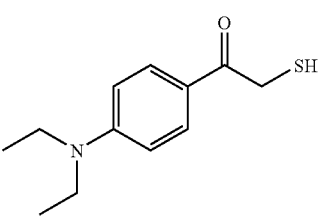

Compound 40

Compound 40: Characterization of 1-(4-Diethylamino-phenyl)-2-mercapto-ethanone
$^1$H-NMR: (400 MHz, CDCl$_3$) 7.83 (dd, 2H), 6.63 (dd, 2H), 3.85 (d, 2H), 3.43 (q, 4H), 2.17 (t, 1H), 1.21 (t, 6H). LC-MS (ES+): 224 [MH]$^+$ m/e.

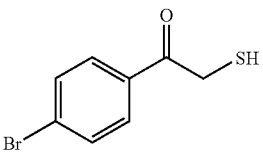

Compound 41

Compound 41: CHaraterization of 1-(4-Bromo-phenyl)-2-mercapto-ethanone
$^1$H-NMR: (400 MHz, CDCl$_3$) 7.83 (m, 2H), 7.64 (m, 2H), 3.92 (d, 2H), 2.11 (t, 1H). LC-MS (ES+): 230, 232 [MH]$^+$ m/e.

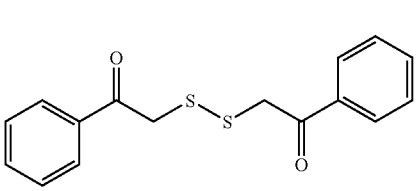

Compound 44

Compound 44: Synthesis of 2-(2-Oxo-2-phenyl-ethyldisulfanyl)-1-phenyl-ethanone
$^1$H-NMR: (400 MHz, CDCl$_3$) 7.95 (d, 4H), 7.61 (t, 2H), 7.49 (t, 4H), 4.22 (s, 4H). LC-MS (ES+): 303 [MH]$^+$ m/e.

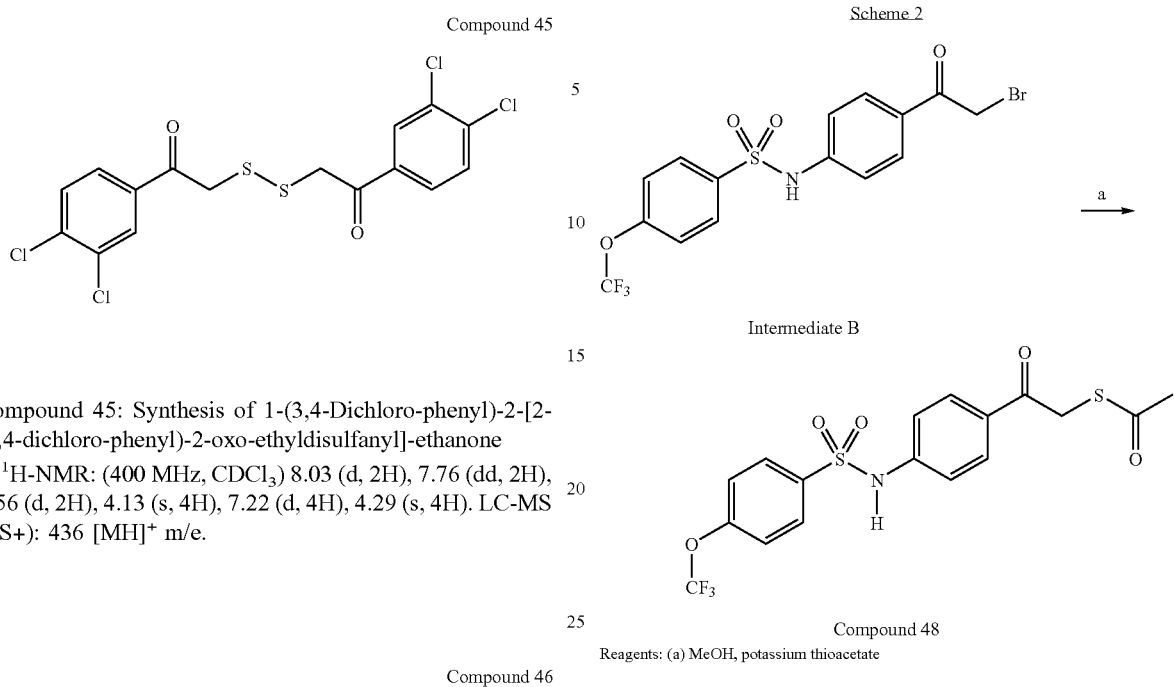

Compound 45: Synthesis of 1-(3,4-Dichloro-phenyl)-2-[2-(3,4-dichloro-phenyl)-2-oxo-ethyldisulfanyl]-ethanone $^1$H-NMR: (400 MHz, CDCl$_3$) 8.03 (d, 2H), 7.76 (dd, 2H), 7.56 (d, 2H), 4.13 (s, 4H), 7.22 (d, 4H), 4.29 (s, 4H). LC-MS (ES+): 436 [MH]$^+$ m/e.

Compound 46: Synthesis of 1-(3,4-Dimethoxy-phenyl)-2-[2—(3,4-dimethoxy-phenyl)2-oxo-ethyldisulfanyl]-ethanone $^1$H-NMR: (400 MHz, CDCl$_3$) 7.55 (m, 4H), 6.87 (d, 2H), 4.15 (s, 4H), 3.95 (s, 6H), 3.94 (s, 6H). LC-MS (ES+): 423 [MH]$^+$ m/e.

Example 5

General Procedure for the Synthesis of Thioesters and an Alternate General

Synthesis of Disulfides

Scheme 2 outlines a general synthesis of thioesters, explicitly exemplified with reference to the preparation of Compound 48. Hydrolysis of thioesters, followed by oxidation, results in a general synthesis of disulfides, explicitly exemplified with reference to the preparation of Compound 47.

Reagents: (a) MeOH, potassium thioacetate

Compound 48: Thioacetic acid S-{2-oxo-2-[4-(4-trifluoromethoxy-benzenesulfonylamino)-phenyl]-ethyl}ester Intermediate B (29 g crude material, 66.18 mmol) was dissolved in methanol (500 ml) before potassium thioacetate (8.23 g, 72.06 mmol) was added as a solid. LC-MS of the resulting yellow solution shows the reaction is complete in minutes. Evaporation of the volatiles leaves a tan residue which was taken up into dichloromethane (100 ml), during which a deposit of disulfide (thioacetic acid) was deposited and filtered. The desired thioester could then be recrystallized from dichloromethane/hexanes (18.52 g, 42.67 mmol, 64%) It had $^1$H-NMR: (DMSO-d$_6$) 11.09 (bs, 1H), 7.98 (d, 2H), 7.92 (d, 2H), 7.59 (d, 2H), 7.24 (d, 2H), 4.42 (s, 2H), 2.36 (s, 3H) ppm. It had LC-MS (ES+): 434 [M]$^+$ m/e.

Compound 47: Corresponding disulfide of Compound 43

Compound 48 (2.3 g, 5.3 mmol) was dissolved in MeOH (50 ml) before solid NaOH was carefully added with vigorous stirring. The resulting yellow solution was then stirred for 2 hours before being neutralized with con. HCl and evaporated to leave a red residue. Water (20 ml) was added and the mixture extracted with EtOAc. The organic fractions were dried over $Na_2SO_4$ and evaporated. The residue was taken up in $CH_2Cl_2$ (50 ml) and stirred while open to the air. The desired disulfide precipitates within hours and is complete overnight yielding a pure solid (1.1 g, 1.41 mmol, 53%). It had identical spectral characteristics as the material obtained in the original synthesis.

Example 9

Inhibition Assays

In vitro HDAC-inhibition Assay:

This assay measures a compound's ability to inhibit acetyl-lysine deacetylation in vitro and was used as both a primary screening method as well as for $IC_{50}$ determinations of confirmed inhibitors. The assay is performed in vitro using an HDAC enzyme source (e.g. partially purified nuclear extract or immunopurified HDAC complexes) and a proprietary fluorescent substrate/developer system (HDAC Quantizyme Fluor de Lys Fluorescent Activity Assay, BIO-MOL). The assay is run in 1,536-well Greiner white-bottom plates using the following volumes and order of addition:

Step 1: Enzyme (2.5 ul) source added to plate (from refrigerated container)
Step 2: Compounds (50 nl) added with pin transfer device
Step 3: *Fluor de Lys* (2.5 ul) substrate added, incubate at RT, 30 minutes
Step 4: Developer (5 ul) solution is added (containing TSA), to stop reaction
Step 5: Plate Reader—data collection The deacetylated fluorophore is excited with 360 nm light and the emitted light (460 nm) is detected on an automated fluorometric plate reader (Aquest, *Molecular Devices*).

Cellular Histone Hyperacetylation Assays:

These two secondary assays evaluates a compound's ability to inhibit HDAC in cells by measuring cellular histone acetylation levels. The cytoblot facilitates quantitative $EC_{50}$ information for cellular HDAC inhibition. Transformed cell lines (e.g. HeLa, A549, MCF-7) are cultured under standard media and culture conditions prior to plating.

For Cytoblot:

Cells (approx. 2,500/well) are allowed to adhere 10-24 hours to wells of a 384-well Greiner PS assay plate in media containing 1-5% serum. Cells are treated with appropriate compound and specific concentrations for 0 to 24 hours. Cells are washed once with PBS (60 ul) and then fixed (95% ethanol, 5% acetic acid or 2% PFA) for 1 minute at RT (30 ul). Cells are blocked with 1% BSA for 1 hour and washed and stained with antibody (e.g. anti-Acetylated Histone H3, *Upstate Biotechnology*), followed by washing and incubation with an appropriate secondary antibody conjugated to HRP or fluorophore. For luminescence assays, signal is generated using Luminol substrate (*Santa Cruz Biotechnology*) and detected using an Aquest plate reader (*Molecular Devices*).

For Immunoblot:

Cells (4×10^5/well) are plated into Corning 6-well dish and allowed to adhere overnight. Cells are treated with compound at appropriate concentration for 12-18 hours at 37 degrees. Cells are washed with PBS on ice. Cells are dislodged with rubber policeman and lysed in buffer containing 25 mM Tris, pH7.6; 150 mM NaCl, 25 mM $MgCl_2$, 1% Tween-20, and nuclei collected by centriguation (7500 g). Nuclei are washed once in 25 mM Tris, pH7.6; 10 mM EDTA, collected by centrifugation (7500 g). Supernatant is removed and histones are extracted using 0.4 M HCl. Samples are centrifuged at 14000 g and supernatants are precipitated in 1 ml cold acetone. The histone pellet is dissolved in water and histones are separated and analyzed by SDS-PAGE Coomassie and immunobloting (anti-acetylated histone antibodies, *Upstate Biotechnology*) using standard techniques.

Differential Cytotoxicity Assay:

HDAC inhibitors display differential cytotoxicity toward certain transformed cell lines. Cells are cultured according to standard ATCC recommended conditions that are appropriate to each cell type. Compounds were tested for their ability to kill different cell types (normal and transformed) using the ATPlite luminescence ATP detection assay system (*Perkin Elmer*). Assays are run in either 384-well or 1536-well Greiner PS plates. Cells (30 ul or 5 ul, respectively) are dispensed using either multichannel pipette for 384-well plates, or proprietary *Kalypsys* bulk liquid dispenser for 1536-well plates. Compounds added using proprietary pin-transfer device (500 nL or 5 nL) and incubated 5 to 30 hours prior to analysis. Luminescence is measured using Aquest plate reader (*Molecular Devices*).

The activity of some of the compounds of the invention are shown in Table 2, below, together with data for positive controls: TSA, HC-toxin, Dioxothiophene & MS-275.

TABLE 2

| Compound Description | in vitro $IC_{50}$ (μM) | % Max Inhibition (in vitro) | Cellular $IC_{50}$ (μM) | % Max. Inhibition (cellular) |
|---|---|---|---|---|
| TSA positive control (published in vitro $IC_{50}$ = 3-6 nM) | <1 | 100 | <1 | 100 |
| HC-toxin positive control (published in vitro $IC_{50}$ = 7-10 nM) | <1 | >75 | N.D. | N.D. |
| Dioxothiophene* | >10 | <50 | N.D. | N.D. |
| MS-275 (clinical compound - benzamide anilide) | >10 | >50 | 1-10 | >75 |
| 1 | 1-10 | >75 | active | N.D. |
| 2 | <1 | >75 | active | N.D. |
| 3 | <1 | >75 | 1-10 | 104 |
| 4 | <1 | >75 | 1-10 | >75 |
| 5 | <1 | >75 | active | N.D. |
| 6 | <1 | >75 | 1-10 | >75 |
| 7 | <1 | >75 | 1-10 | >75 |
| 8 | <1 | >75 | active | N.D. |
| 9 | <1 | >75 | active | N.D. |
| 10 | 1-10 | >75 | active | N.D. |
| 11 | 1-10 | >50 | active | N.D. |
| 12 | 1-10 | >75 | N.D. | N.D. |
| 13 | 1-10 | >75 | active | N.D. |
| 14 | >10 | >75 | >10 | <50 |
| 15 | 1-10 | >75 | 1-10 | >75 |
| 16 | 1-10 | >75 | active | N.D. |
| 17 | >10 | >75 | active | N.D. |
| 18 | >10 | >75 | active | N.D. |
| 19 | >10 | >75 | 1-10 | >50 |
| 20 | >10 | >75 | active | N.D. |
| 21 | >10 | >75 | 1-10 | >75 |
| 22 | >10 | <50 | 1-10 | <50 |
| 23 | >10 | >50 | active | N.D. |
| 24 | >10 | >50 | active | N.D. |
| 25 | >10 | <50 | active | N.D. |

TABLE 2-continued

| Compound Description | in vitro IC$_{50}$ (μM) | % Max Inhibition (in vitro) | Cellular IC$_{50}$ (μM) | % Max. Inhibition (cellular) |
|---|---|---|---|---|
| 26 | 1-10 | >75 | <1 | >75 |
| 27 | 1-10 | >75 | 1-10 | >75 |
| 29 | 1-10 | >75 | 1-10 | >75 |
| 30 | 1-10 | >75 | 1-10 | >75 |
| 31 | 1-10 | >75 | 1-10 | >75 |
| 32 | <1 | >75 | >10 | >50 |
| 33 | <1 | >75 | >10 | >75 |
| 34 | <1 | >75 | 1-10 | >75 |
| 41 | <1 | >75 | active | >75 |
| 42 | 1-10 | >75 | >10 | >75 |
| 47 | <1 | >75 | <1 | >75 |
| 48 | <1 | >75 | <1 | >75 |

"N.D." indicates not determined because max inhibition was not reached at highest concentration tested.
"Active" means the compound showed inhibitory activity but the cellular IC$_{50}$ could not be determined Exemplary compounds and pharmaceutically acceptable esters or prodrugs thereof according to the invention include, but are not limited to, illustrative disulfide dimers, mercaptans, and thioesters as shown herein. Exemplary mercaptans of compounds according to structures I, II, or IV include the following:

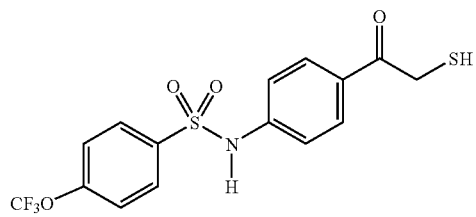

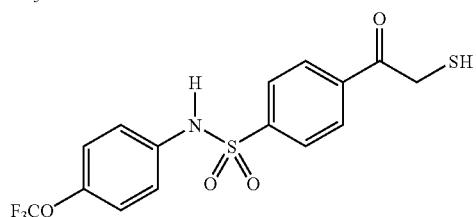

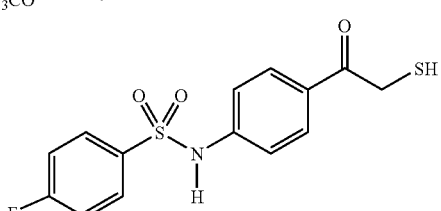

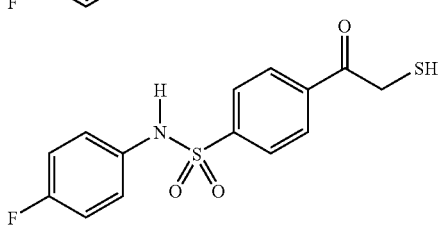

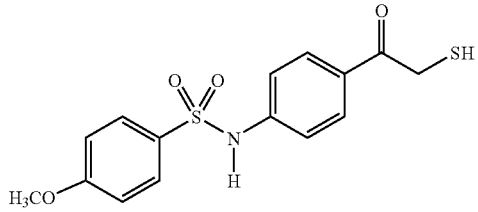

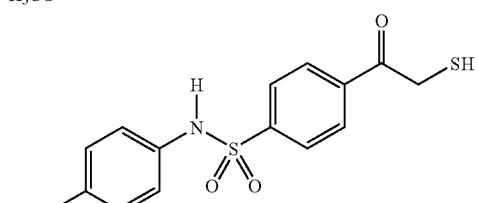

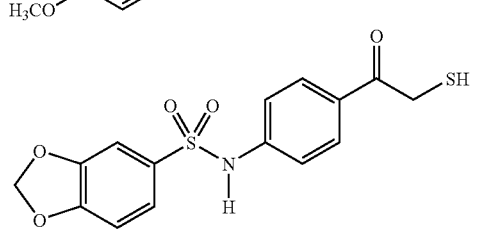

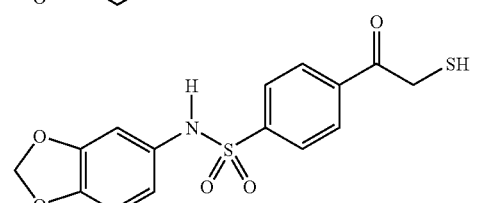

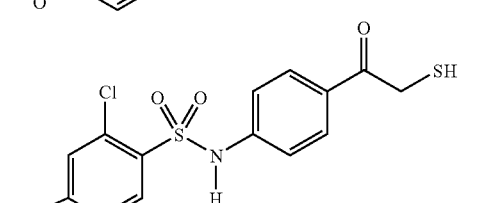

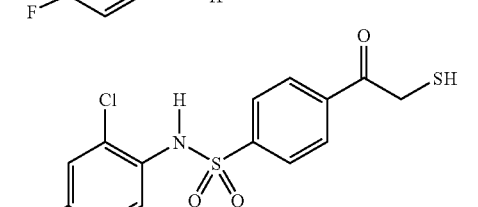

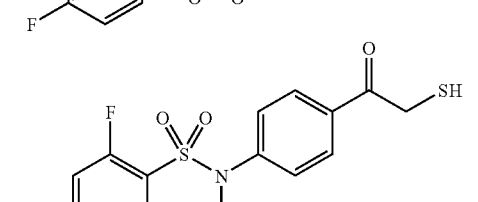

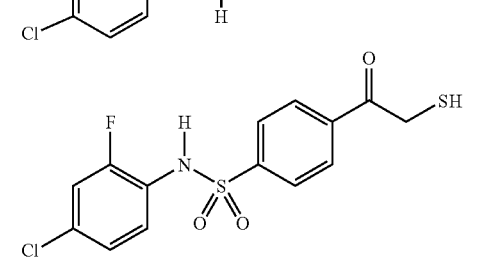

-continued
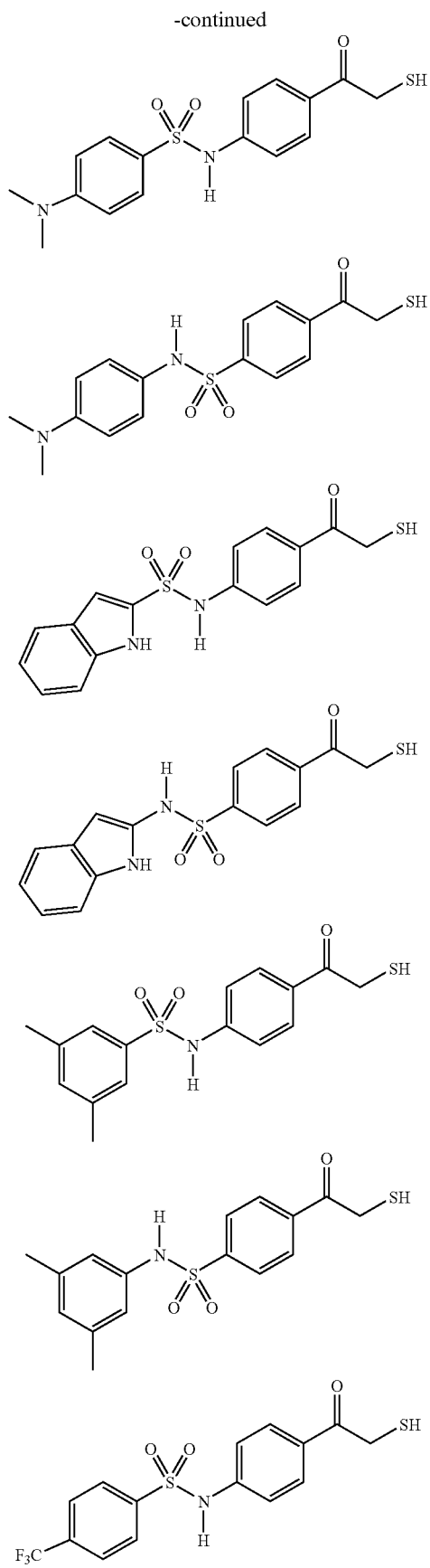
-continued
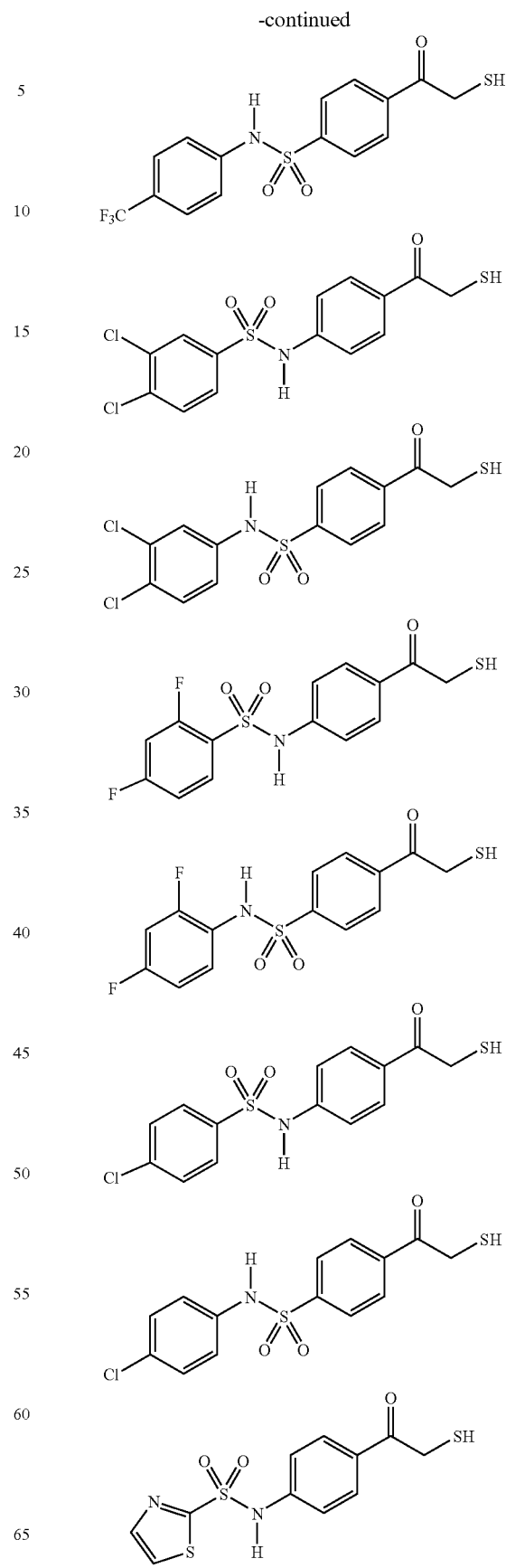

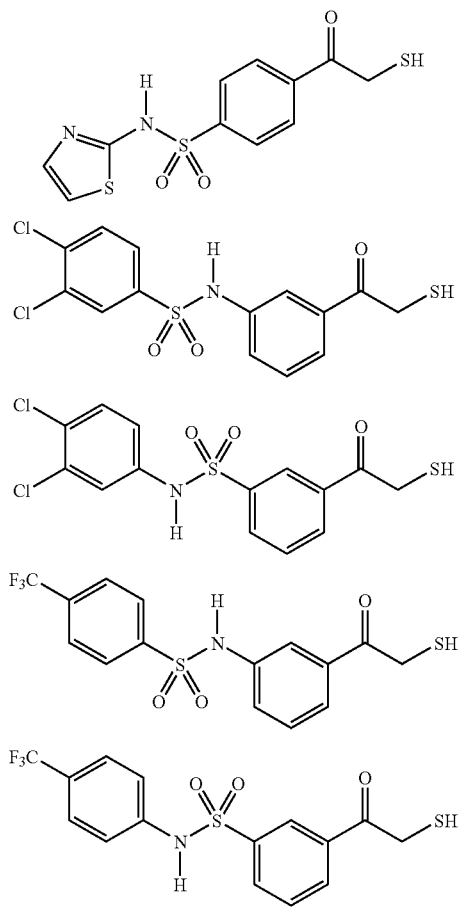
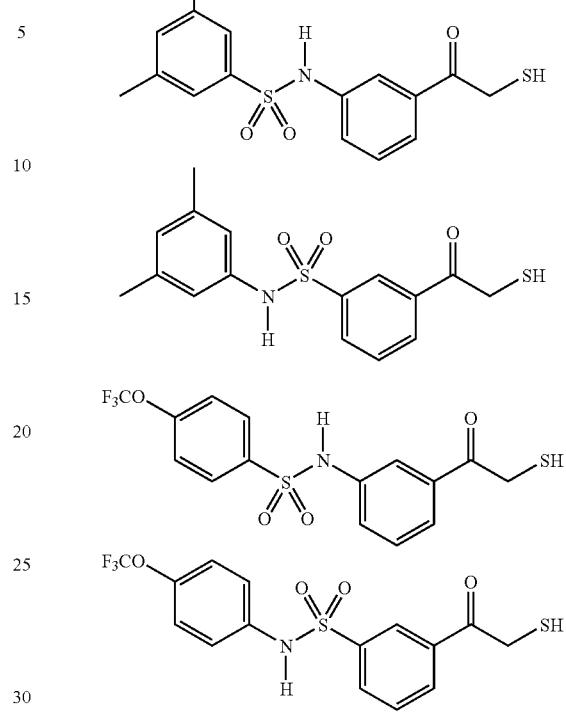
Preferred disulfides are symmetric and in a preferred embodiment, compounds of structure III are provided by the invention wherein T=S, all R6 are equivalent, all R7 are equivalent, and R15=R16 or compounds of structure IV wherein R8 is defined so as to form a symmetric disulfide dimer. Exemplary disulfides according to structures I, III, and IV include the following:
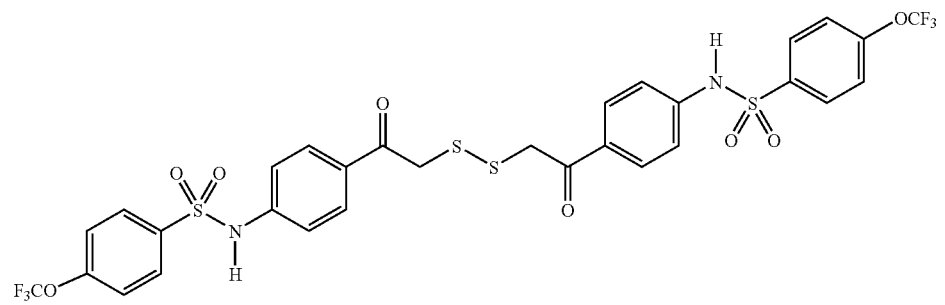
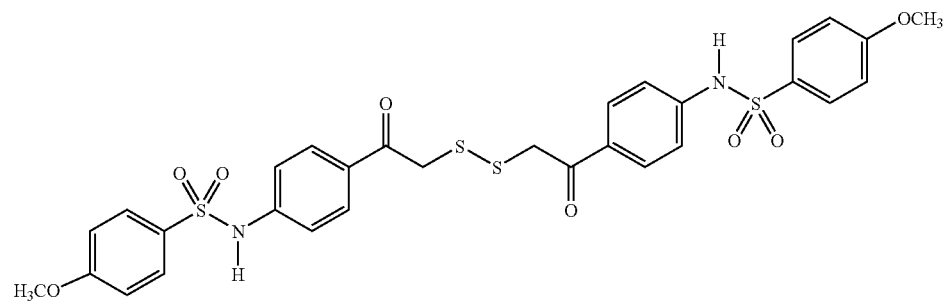

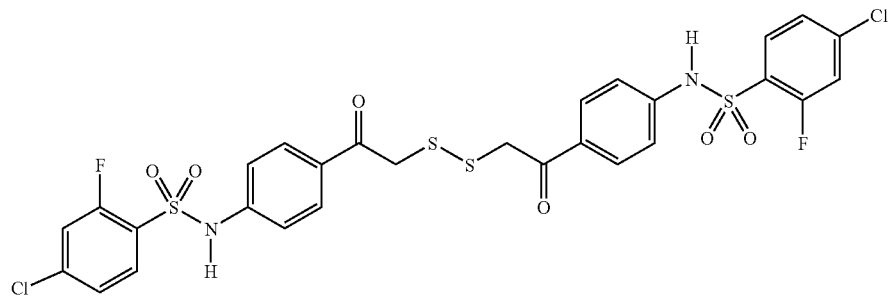
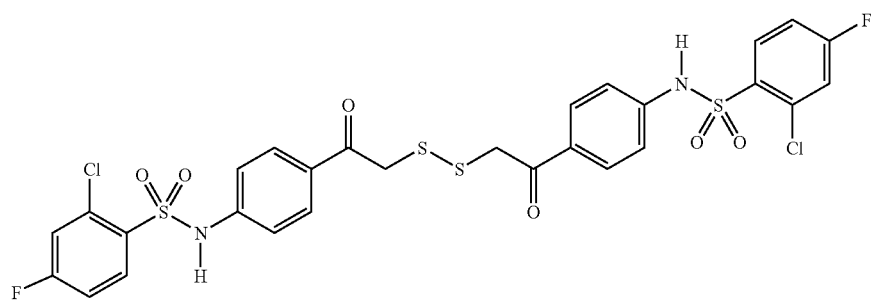
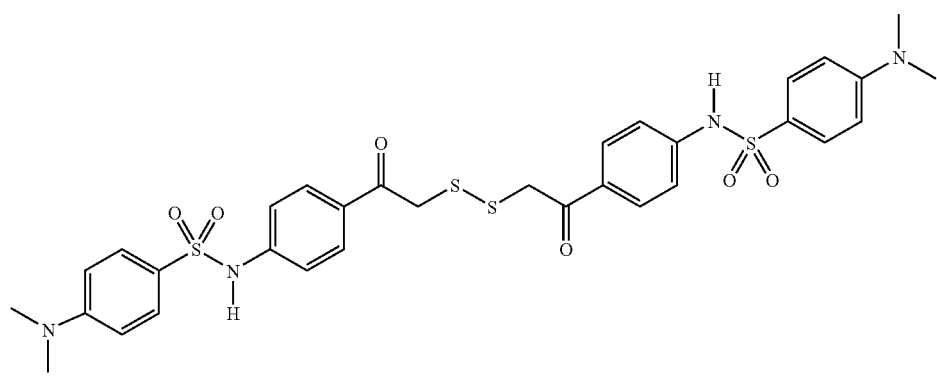
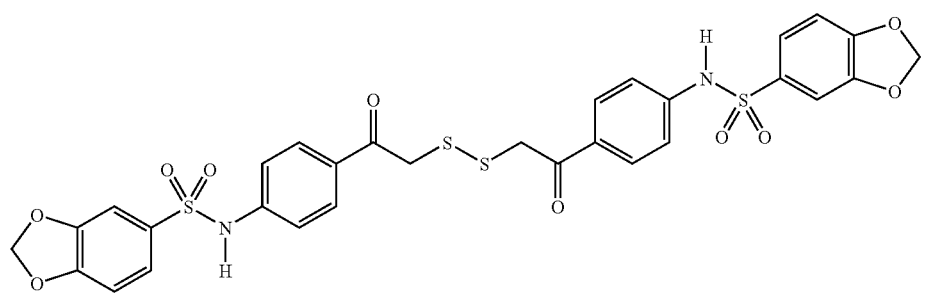
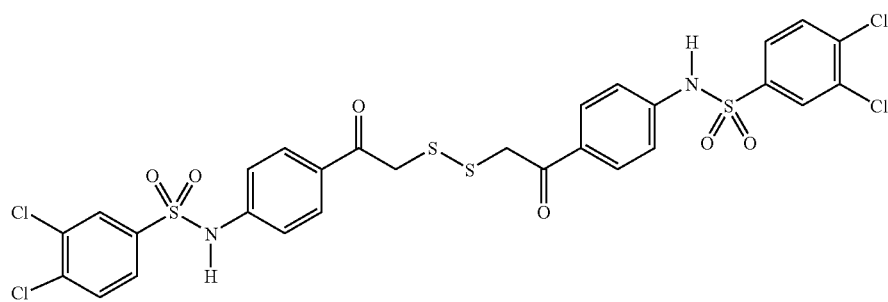

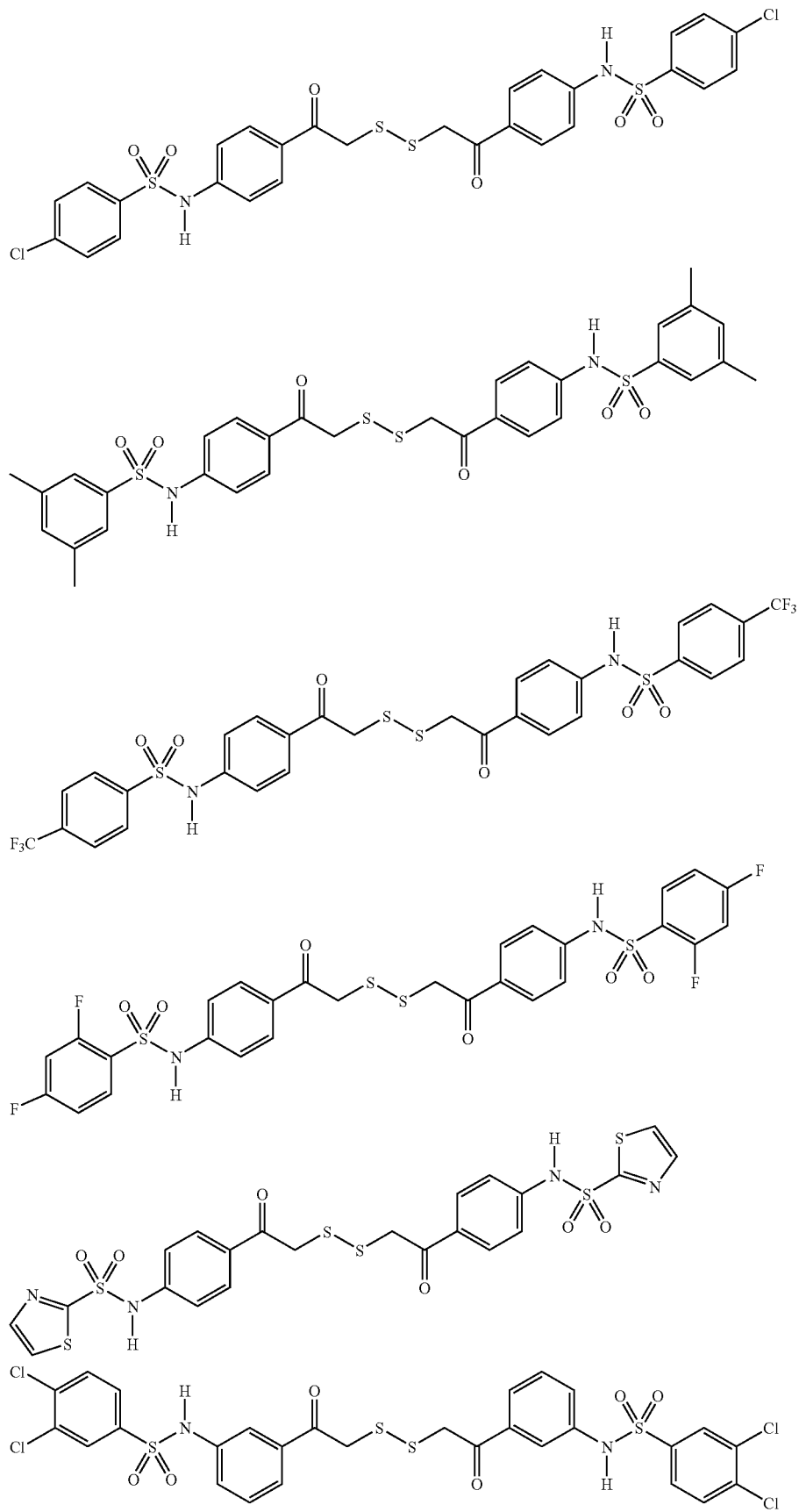

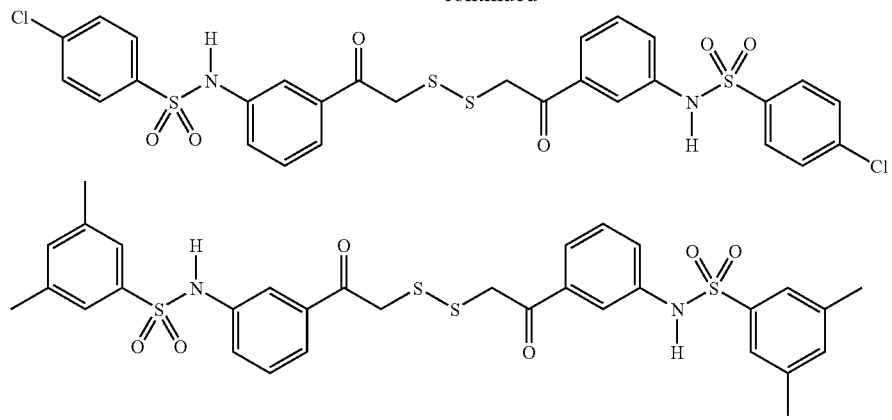
Preferred thioesters of the invention include compounds of structures I, II, and IV wherein thioester hydrolysis yields an organic acid which is pharmaceutically acceptable including, but not limited to the following exemplary thioesters:
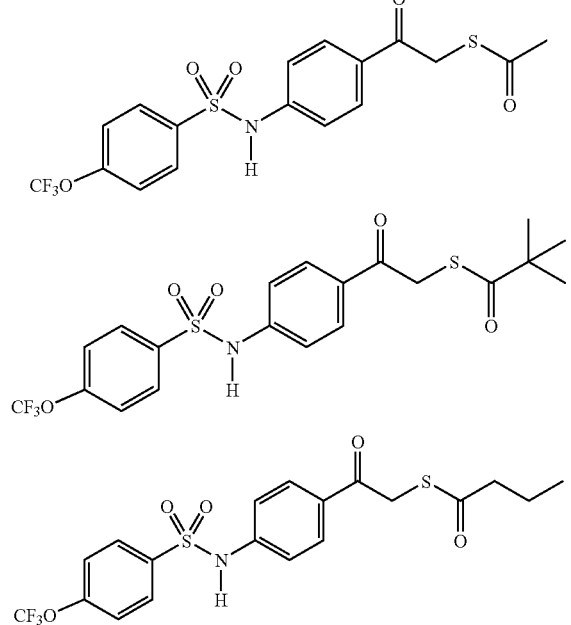
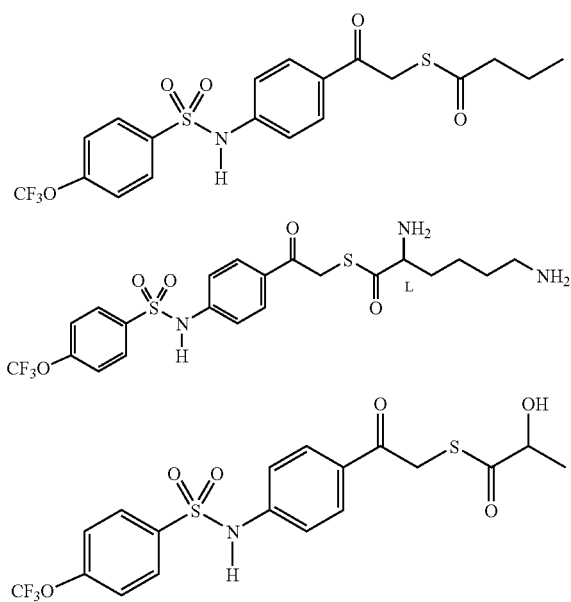
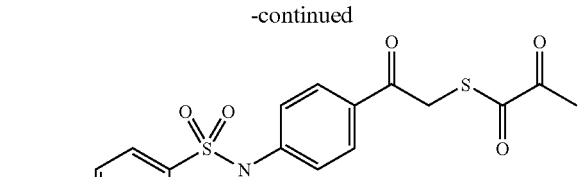
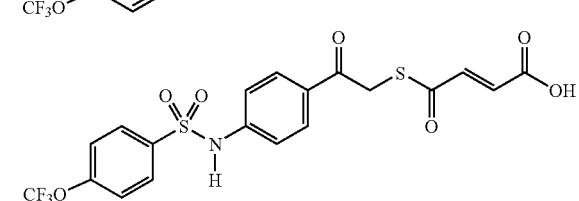
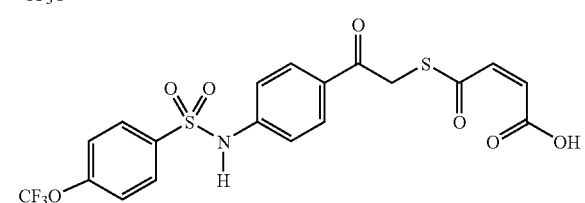
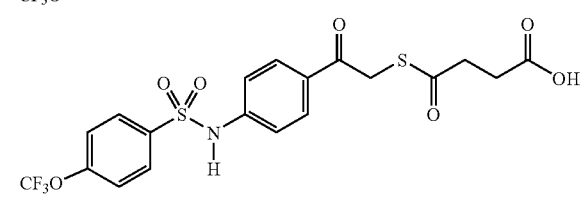
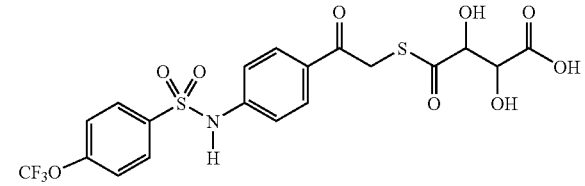
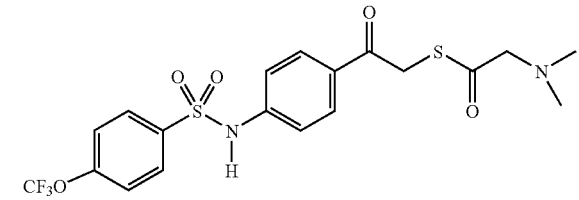

71
-continued
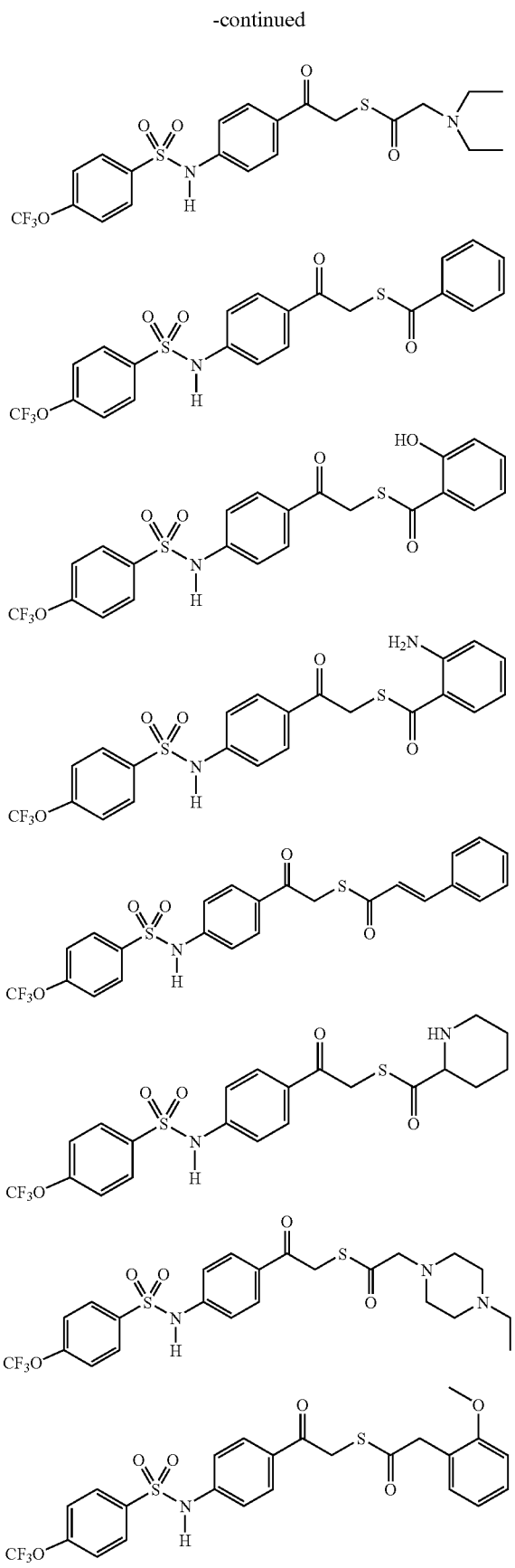
72
-continued
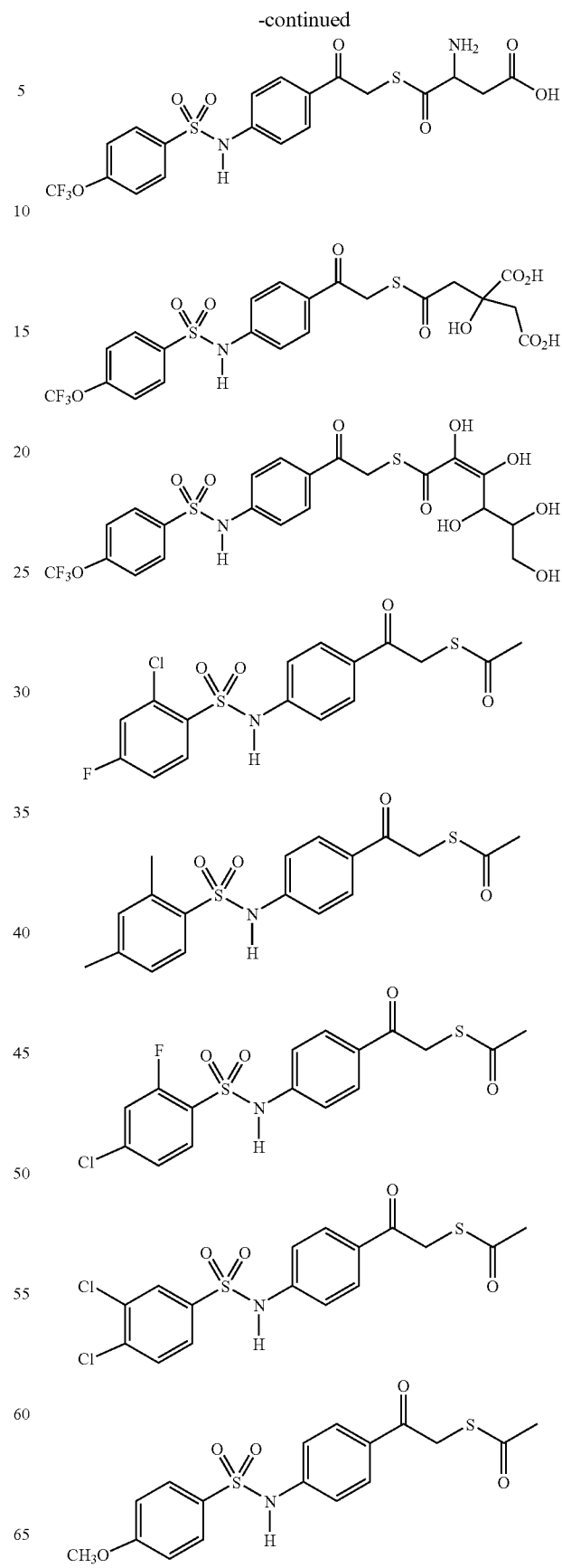

-continued

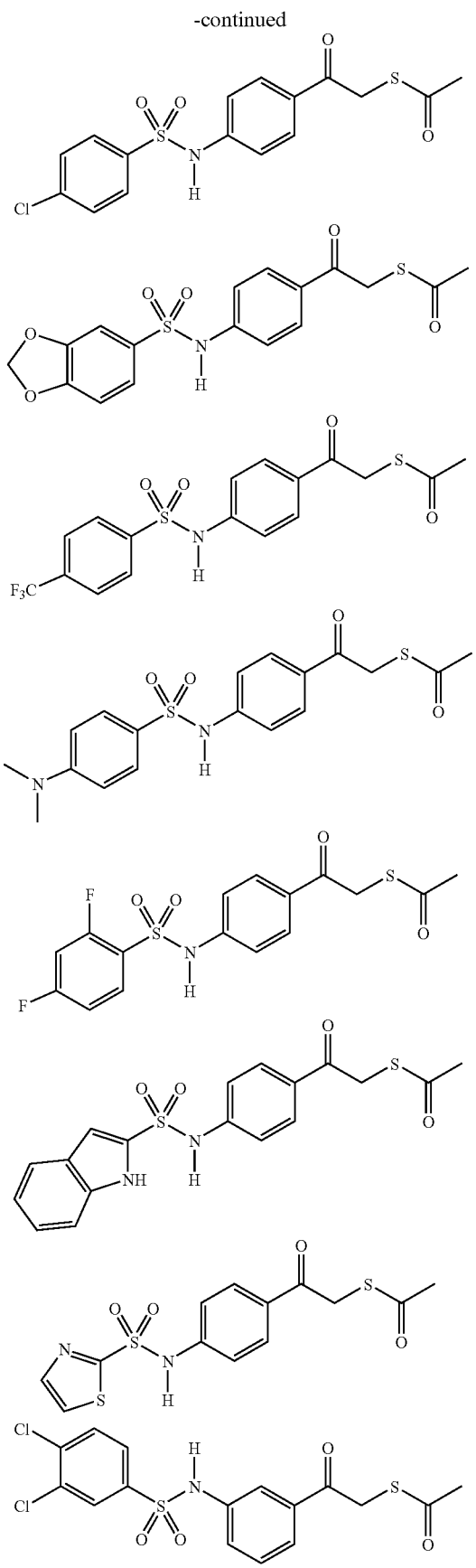

-continued

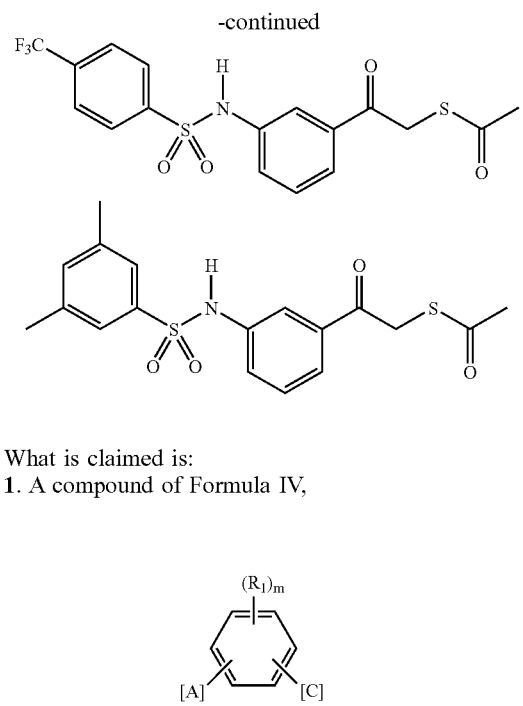

What is claimed is:
1. A compound of Formula IV,

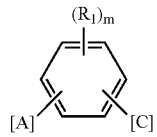

(IV)

or a pharmaceutically acceptable salt, amide, ester, or prodrug thereof,
wherein
a) [A] is

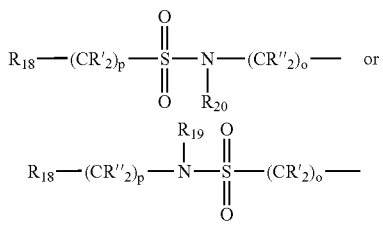

wherein o and p are each independently 0, 1, 2, or 3;
R' and R" are each independently selected from the group consisting of hydrogen and lower alkyl;
$R_{18}$ is a lower heteroalkyl, a five-, six-, seven-, or eight-membered monocyclic carbocyclic aliphatic ring, or a six-membered monocyclic aryl ring, each optionally substituted with one or more substituents selected from the group consisting of
  i) optionally substituted $C_1$-$C_8$ straight-chain, branched, or cyclic saturated or unsaturated alkyl;
  ii) an alkoxy of formula —$(X_1)_{n1}$—O—$X_2$, where
    $X_1$ is selected from the group consisting of lower alkylene, lower alkenylene, lower alkynylene, and aryl;
    $X_2$ is selected from the group consisting of hydrogen, lower alkyl, lower perhaloalkyl, and aryl; and
    n1 is 0, 1, 2 or 3;
  iii) halogen, partially halogenated alkyl, or perhaloalkyl;
  iv) cyano;
  v) nitro;

vi) an amino of formula —$(X_3)_{n3}$—$NX_4X_5$, where
  $X_3$ is selected from the group consisting of lower alkylene, lower alkenylene, lower alkynylene, and aryl;
  $X_4$ and $X_5$ are each independently selected from the group consisting of hydrogen, lower alkyl, and aryl; and
  n3 is 0 or 1;
vii) a thioether or thiol of formula —$(X_6)_{n6}$—S—$X_7$, where
  $X_6$ is selected from the group consisting of lower alkylene, lower alkenylene, lower alkynylene, and aryl;
  $X_7$ is selected from the group consisting of hydrogen, lower alkyl, perfluoroalkyl, and aryl; and
  n6 is 0, 1, 2, or 3; and
viii) an amide of formula —$(X_7)_{n7}$—NH—C(O)—$X_8$ or —$(X_9)_{n9}$—C(O)—NH—$X_{10}$
  $X_7$ and $X_9$ are each independently selected from the group consisting of lower alkylene, lower alkenylene, lower alkynylene, and aryl;
  $X_8$ is selected from the group consisting of hydrogen, lower alkyl, lower alkenyl, lower heteroalkyl, aryl, hydroxy, alkoxy, and amide; and
  $X_{10}$ is selected from the group consisting of hydrogen, lower alkyl, lower alkenyl, lower heteroalkyl, and aryl;
  n7 and n9 are each independently is 0 or 1;
$R_{19}$ is selected from the group consisting of H and $C_{1-5}$ alkyl;
$R_{20}$ is H or $C_{1-5}$ alkyl;
each $R_1$ is each independently selected from the group consisting of
  i) hydrogen;
  ii) lower alkyl;
  iii) lower alkylene;
  iv) halogen, partially halogenated alkyl, or perhaloalkyl; and
  v) an alkoxy or perhaloalkoxy;
c) [C] is $R_8$ is selected from the group consisting of
i) hydrogen;
ii) optionally substituted $C_1$-$C_8$ straight-chain, branched, or cyclic saturated or unsaturated alkyl;
iii) cyano; and
iv) optionally substituted acyl of the formula —$C(O)R_E$, wherein $HOC(O)R_E$ is selected from the group consisting of N,N-diethylglycine; 4-ethylpiperazinoacetic acid; ethyl 2-methoxy-2-phenylacetic acid; N,N-dimethylglycine; (nitrophenoxysulfonyl) benzoic acid, acetic acid, maleic acid, fumaric acid, benzoic acid, tartaric acid, glutamic acid, aspartic acid, proline, D-amino acids, butyric acid, palmitic acid, stearic acid, oleic acid, pipecolic acid, phosphonic acid, phosphoric acid, pivalate (trimethylacetic acid), succinic acid, cinnamic acid, anthranilic acid, salicylic acid, lactic acid, and pyruvic acids;

v) or $R_8$ is equivalent to the balance of Formula IV to form a disulfide dimer;

$R_6$ and $R_7$ are each independently selected from the group consisting of hydrogen and lower alkyl; and m is 0 to 2.

2. The compound of claim 1, wherein $R_{19}$ and $R_{20}$ are each independently H or $C_{1-5}$ alkyl, and o and p are 0.

3. The compound of claim 1, wherein $R_{18}$ is optionally substituted phenyl.

4. The compound of claim 1, wherein $R_8$ is H and the compound is selected from the group of compounds consisting of -continued
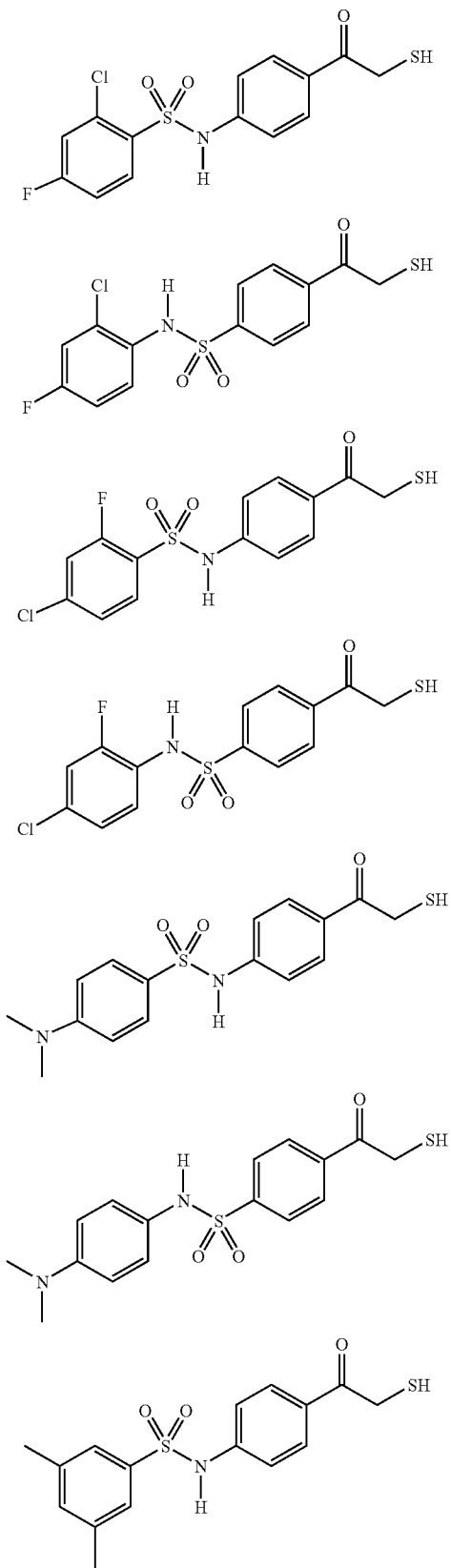
-continued
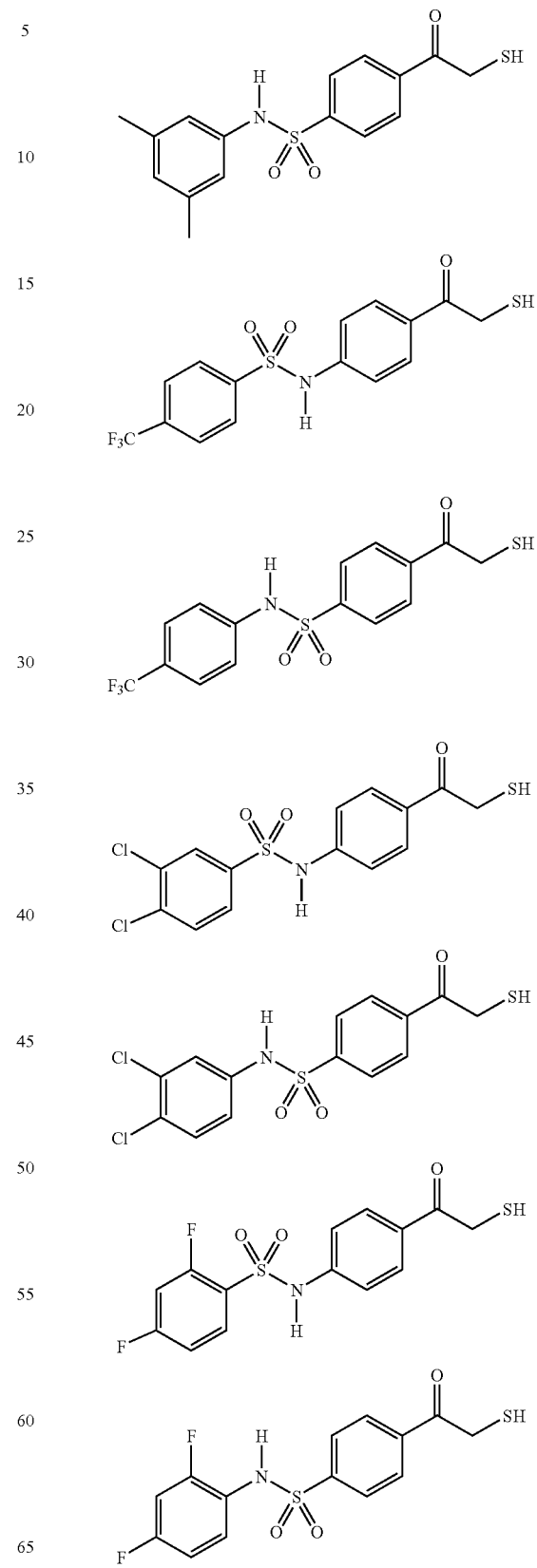

-continued
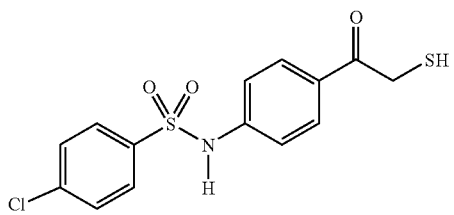
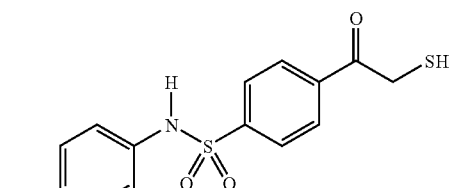
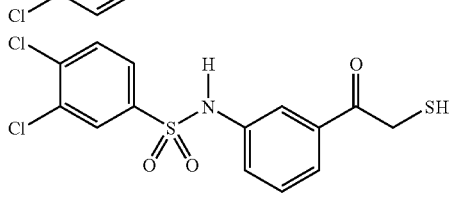
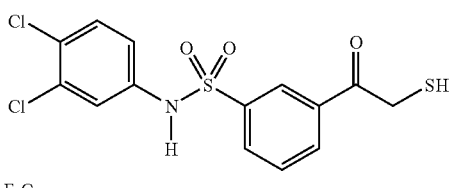
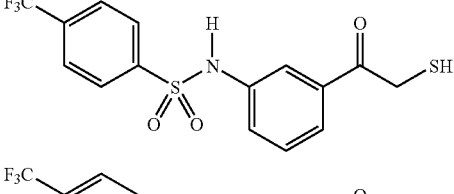
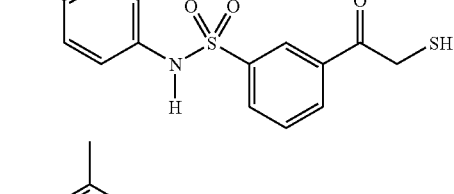
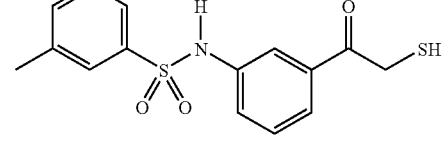
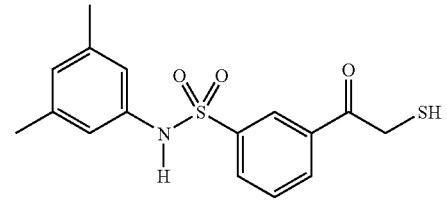
and
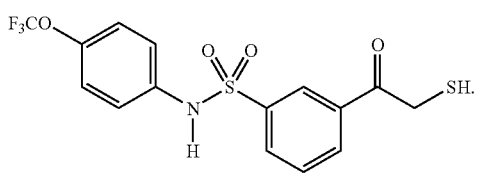
5. The compound of claim 1, wherein $R_8$ is an optionally substituted acyl and the compound has a structure selected from the group consisting of
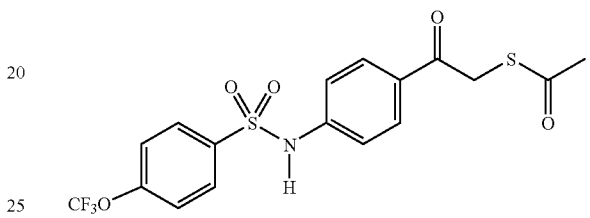
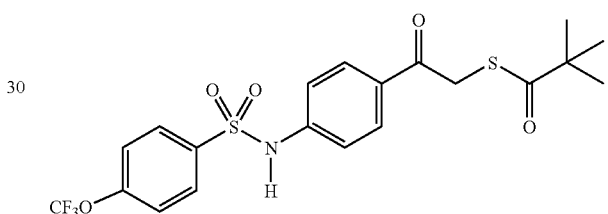
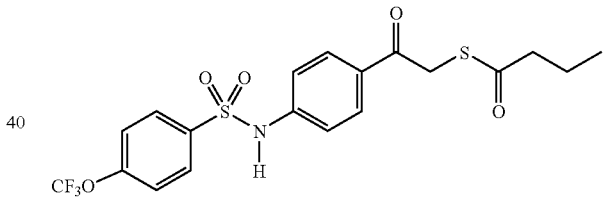
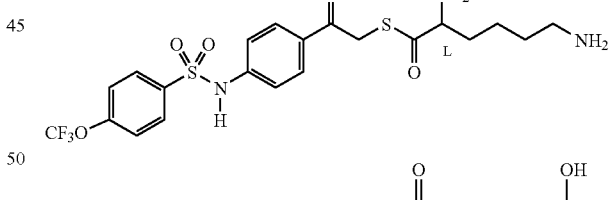
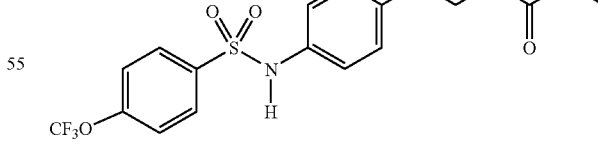
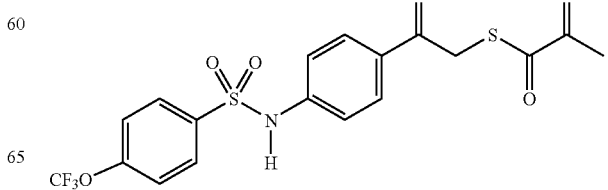

-continued
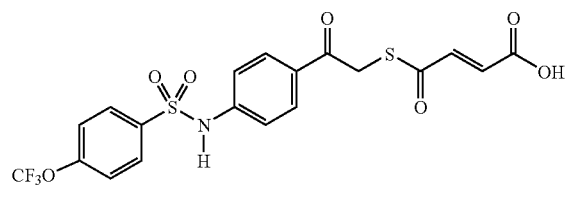
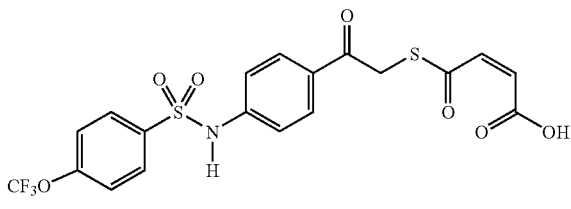
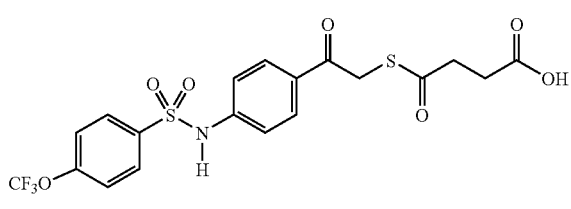
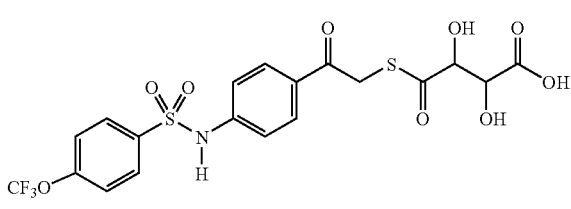
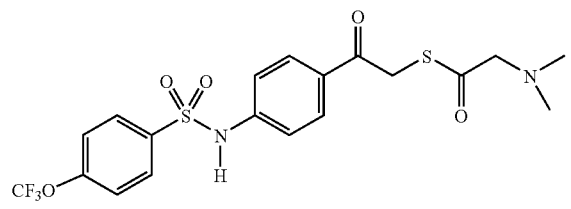
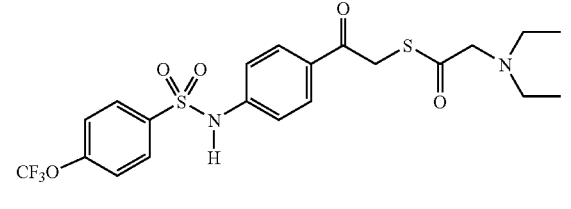
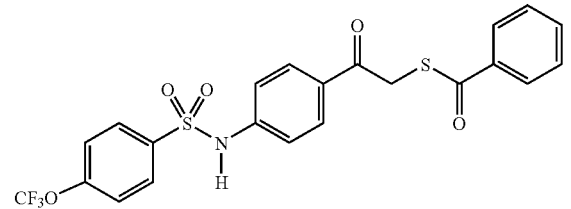
-continued
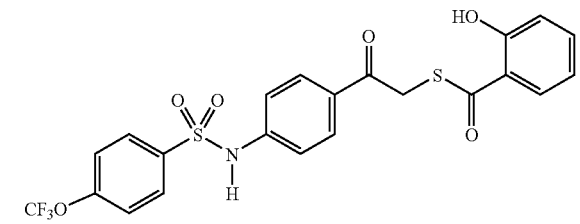
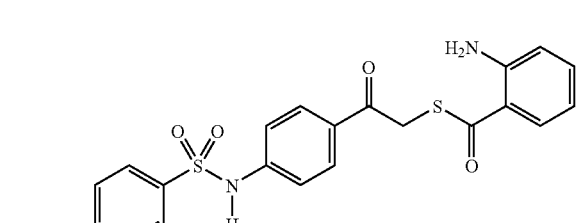
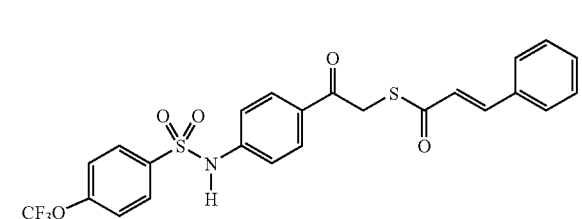
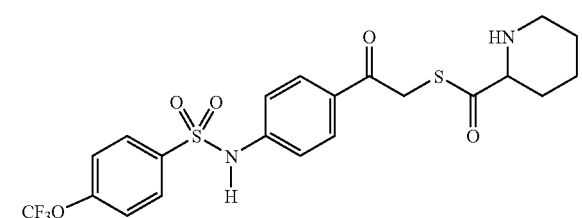
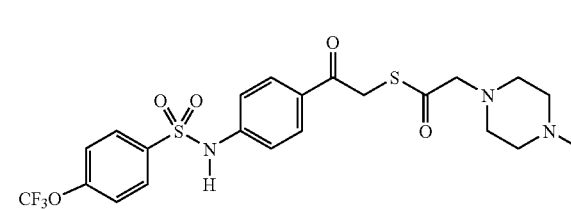
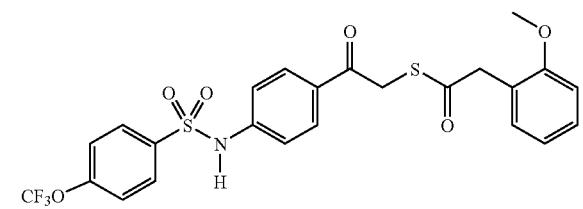
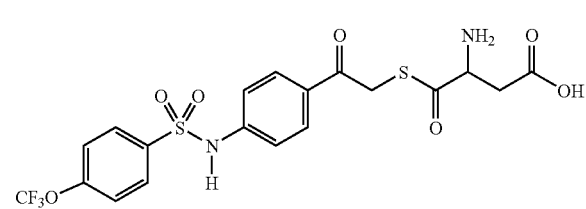

-continued
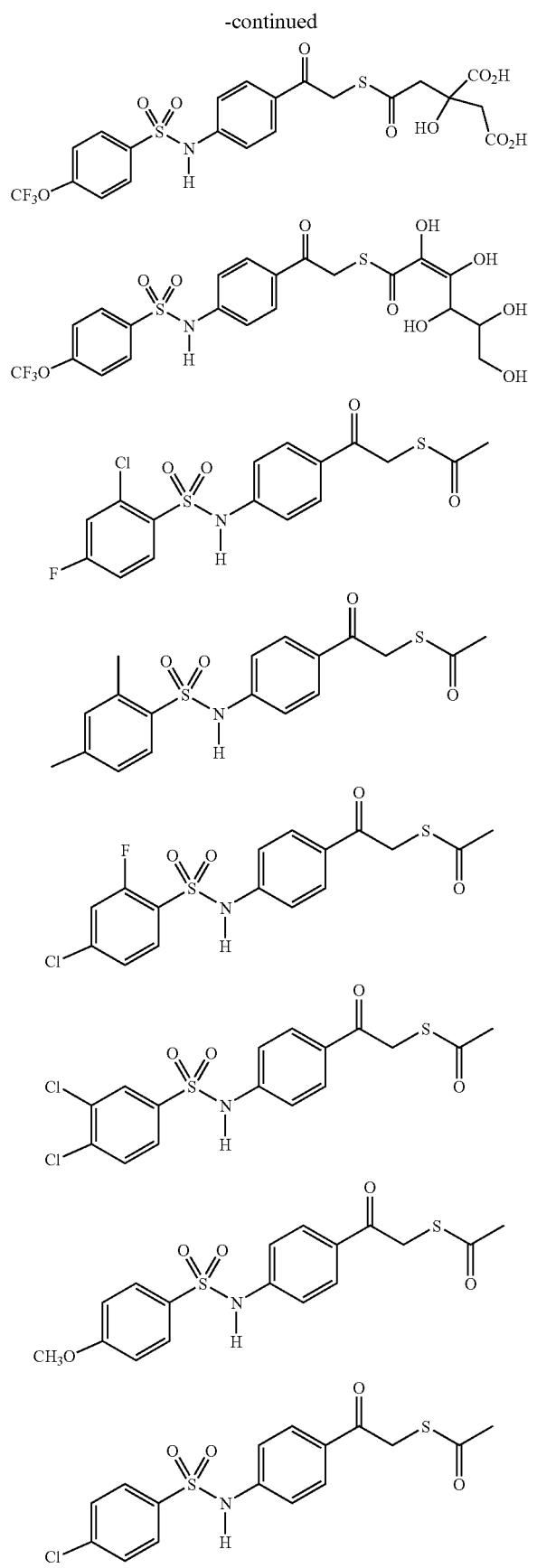
-continued
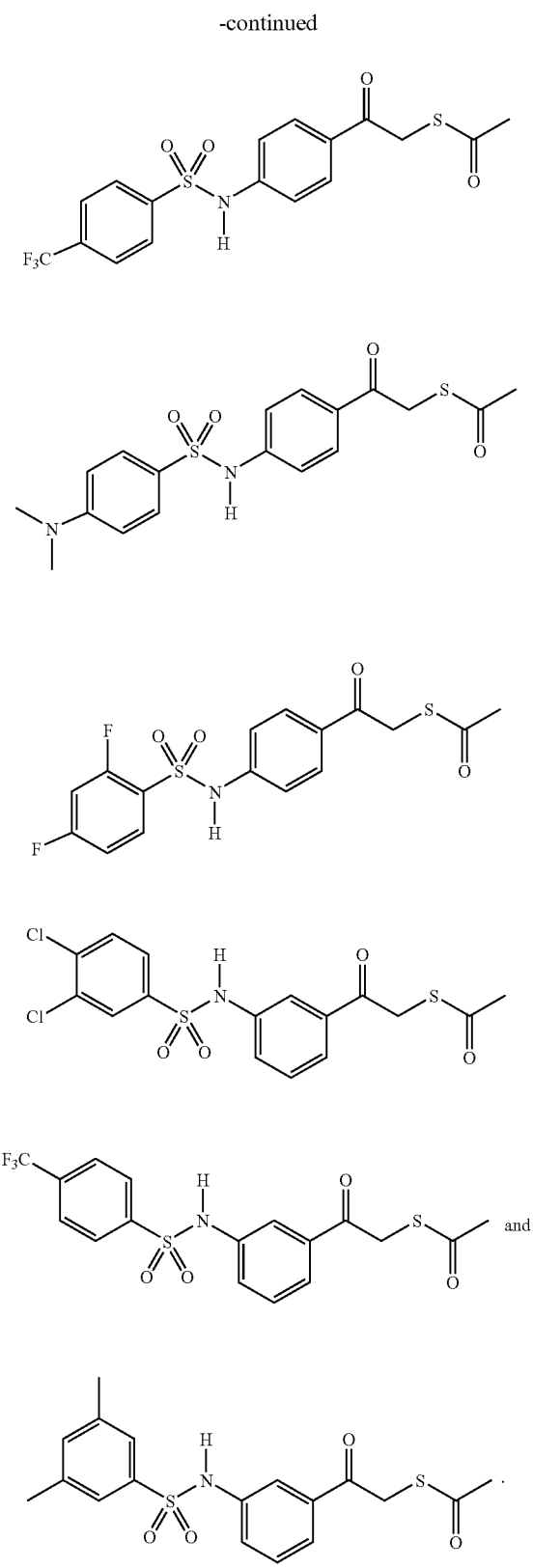
6. The compound of claim 1, wherein $R_8$ is equivalent to the balance of structure IV so as to form a disulfide dimer and the compound has a structure selected from the group consisting of

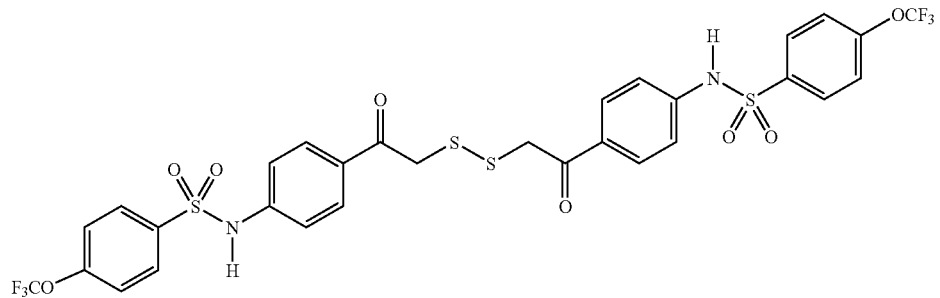
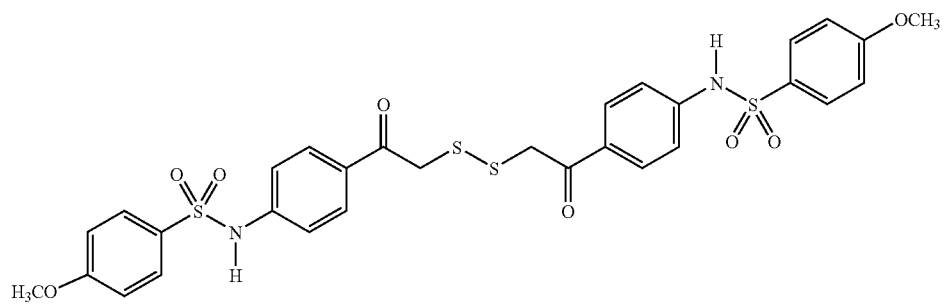
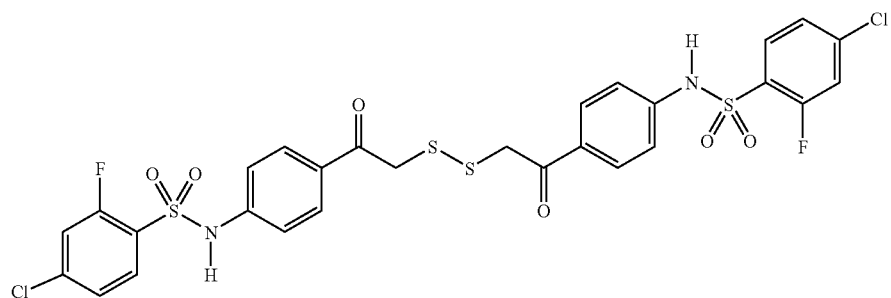
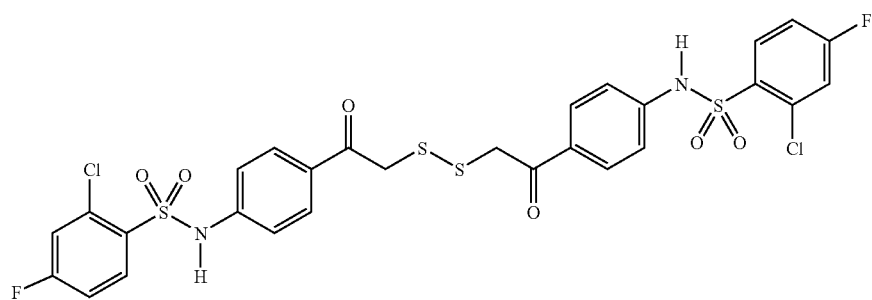
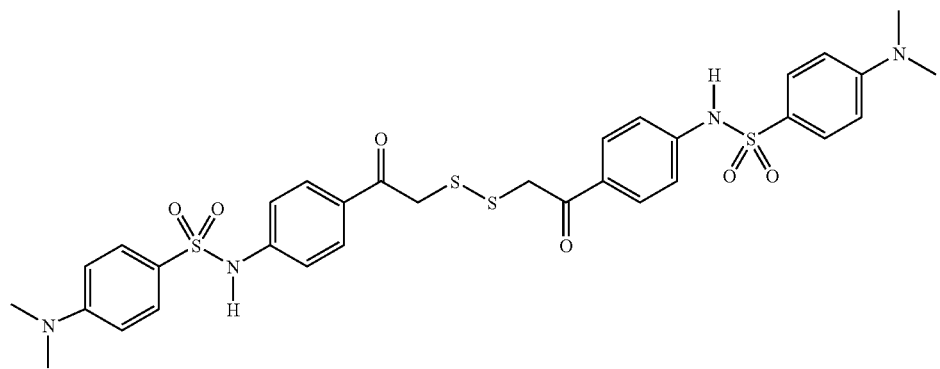

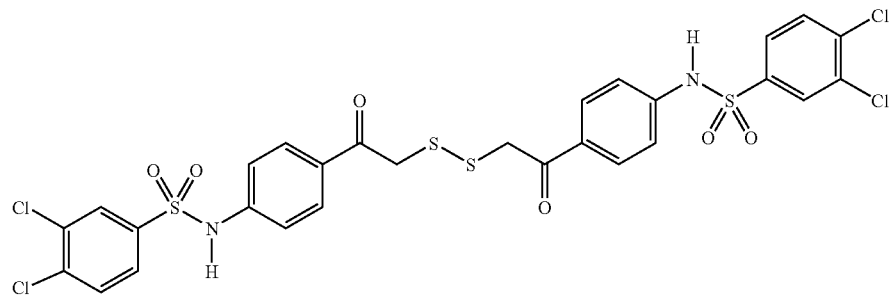
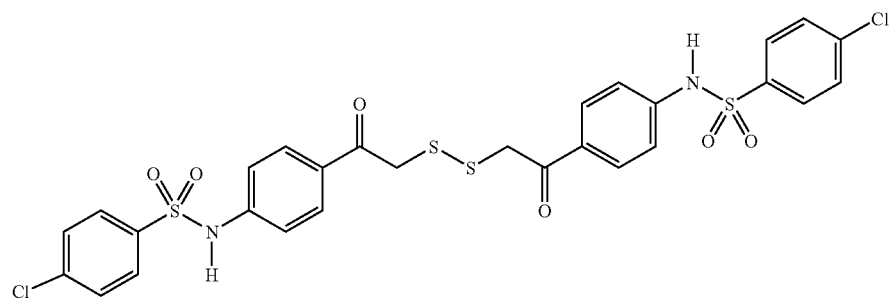
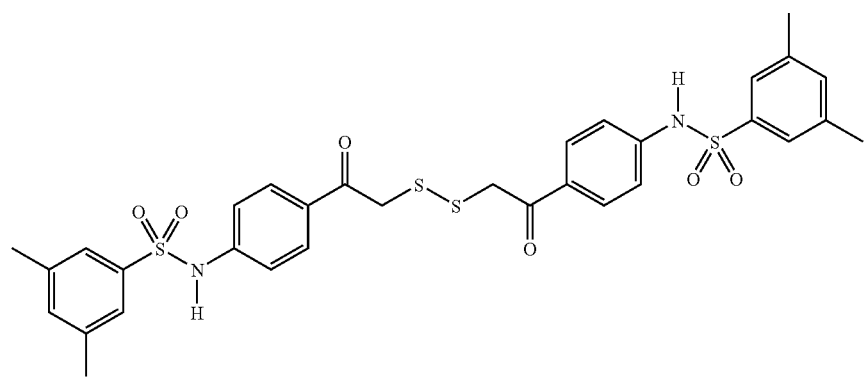
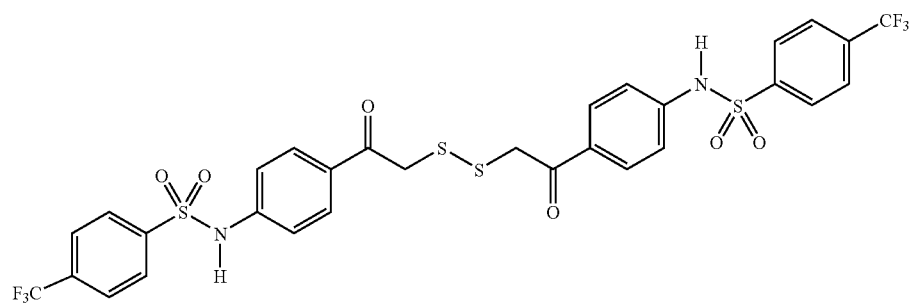
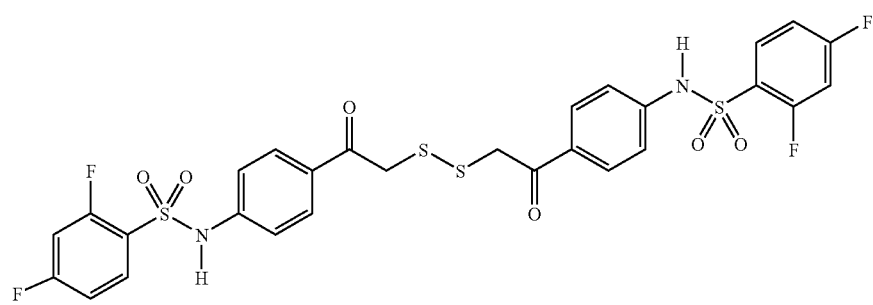

-continued

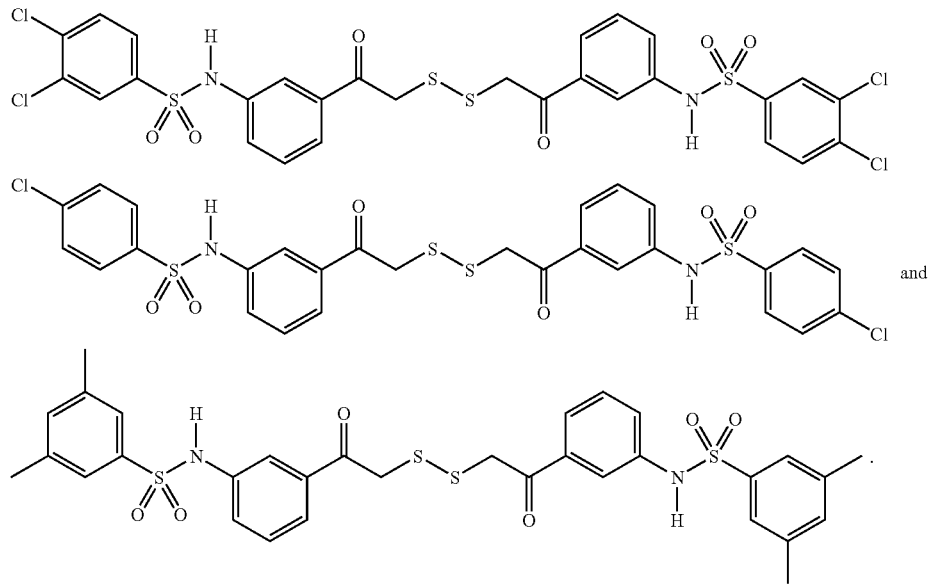

7. A pharmaceutical composition comprising a compound of Formula IV,

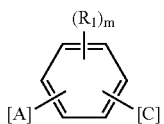

or a pharmaceutically acceptable salt, amide, ester, or prodrug thereof,
wherein
a) [A] is

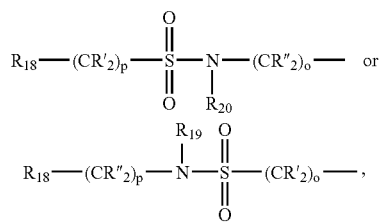

wherein o and p are each independently 0, 1, 2, or 3;
R' and R" are each independently selected from the group consisting of hydrogen and lower alkyl;
$R_{18}$ is a lower alkyl, lower heteroalkyl, a five-, six-, seven-, or eight-membered monocyclic carbocyclic aliphatic ring, or a six-membered monocyclic aryl ring, each optionally substituted with one or more substituents selected from the group consisting of
  i) optionally substituted $C_1$-$C_8$ straight-chain, branched, or cyclic saturated or unsaturated alkyl;
  ii) an alkoxy of formula —$(X_1)_{n1}$—O—$X_2$, where
    $X_1$ is selected from the group consisting of lower alkylene, lower alkenylene, lower alkynylene, and aryl;
    $X_2$ is selected from the group consisting of hydrogen, lower alkyl, lower perhaloalkyl, and aryl; and
    n1 is 0, 1, 2 or 3;
  iii) halogen, partially halogenated alkyl, or perhaloalkyl;
  iv) cyano;
  v) nitro;
  vi) an amino of formula —$(X_3)_{n3}$—$NX_4X_5$, where
    $X_3$ is selected from the group consisting of lower alkylene, lower alkenylene, lower alkynylene, and aryl;
    $X_4$ and $X_5$ are each independently selected from the group consisting of hydrogen, lower alkyl, and aryl; and
    n3 is 0 or 1;
  vii) a thioether or thiol of formula —$(X_6)_{n6}$—S—$X_7$;
    $X_6$ is selected from the group consisting of lower alkylene, lower alkenylene, lower alkynylene, and aryl;
    $X_7$ is selected from the group consisting of hydrogen, lower alkyl, perfluoroalkyl, and aryl;
    n6 is 0, 1, 2, or 3;
  viii) an amide of formula —$(X_7)_{n7}$—NH—C(O)—$X_8$ or —$(X_9)_{n9}$—C(O)—NH—$X_{10}$, where
    $X_7$ and $X_9$ are each independently selected from the group consisting of lower alkylene, lower alkenylene, lower alkynylene, and aryl;
    $X_8$ is selected from the group consisting of hydrogen, lower alkyl, lower alkenyl, lower heteroalkyl, aryl, hydroxy, alkoxy, and amide;
    $X_{10}$ is selected from the group consisting of hydrogen, lower alkyl, lower alkenyl, lower heteroalkyl, and aryl; and
    n7 and n9 are each independently is 0 or 1;

$R_{19}$ is selected from the group consisting of H and $C_{1-5}$ alkyl; and $R_{20}$ is H or $C_{1-5}$ alkyl;

b) each $R_1$ is each independently selected from the group consisting of
  i) hydrogen;
  ii) lower alkyl;
  iii) lower alkylene;
  iv) halogen, partially halogenated alkyl, or perhaloalkyl;
  v) an alkoxy or perhaloalkoxy;

c) [C] is

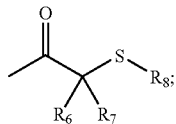

$R_8$ is selected from the group consisting of
  i) hydrogen;
  ii) optionally substituted $C_1$-$C_8$ straight-chain, branched, or cyclic saturated or unsaturated alkyl;
  iii) cyano; and
  iv) optionally substituted acyl of the formula —$C(O)R_E$, wherein $HOC(O)R_E$ is selected from the group consisting of N,N-diethylglycine; 4-ethylpiperazinoacetic acid; ethyl 2-methoxy-2-phenylacetic acid; N,N-dimethylglycine; (nitrophenoxysulfonyl)benzoic acid, acetic acid, maleic acid, fumaric acid, benzoic acid, tartaric acid, glutamic acid, aspartic acid, proline, D-amino acids, butyric acid, palmitic acid, stearic acid, oleic acid, pipecolic acid, phosphonic acid, phosphoric acid, pivalate (trimethylacetic acid), succinic acid, cinnamic acid, anthranilic acid, salicylic acid, lactic acid, and pyruvic acids;
  v) or $R_8$ is equivalent to the balance of Formula IV to form a disulfide dimer; and wherein $R_6$ and $R_7$, are each independently selected from the group consisting of hydrogen and lower alkyl; and m is 0 to 2.

8. The pharmaceutical composition as recited in claim 7 wherein $R_{19}$ and $R_{20}$ are each independently H or $C_{1-5}$ alkyl, and o and p are 0.

9. The pharmaceutical composition as recited in claim 7, wherein $R_{18}$ is optionally substituted phenyl.

10. The pharmaceutical composition as recited in claim 7 together with at least one pharmaceutically acceptable carrier, diluent or excipient.

* * * * *